US010750976B1

(12) United States Patent
McLane

(10) Patent No.: US 10,750,976 B1
(45) Date of Patent: Aug. 25, 2020

(54) DIGITAL STETHOSCOPE FOR COUNTING COUGHS, AND APPLICATIONS THEREOF

(71) Applicant: Sonavi Labs, Inc., Baltimore, MD (US)

(72) Inventor: Ian Mitra McLane, Baltimore, MD (US)

(73) Assignee: Sonavi Labs, Inc., Baltimore, MD (US)

( * ) Notice: Subject to any disclaimer, the term of this patent is extended or adjusted under 35 U.S.C. 154(b) by 0 days.

(21) Appl. No.: 16/659,371

(22) Filed: Oct. 21, 2019

(51) Int. Cl.
| A61B 5/00 | (2006.01) |
| A61B 5/08 | (2006.01) |
| A61B 7/00 | (2006.01) |
| A61B 7/04 | (2006.01) |
| A61B 5/0205 | (2006.01) |

(52) U.S. Cl.
CPC .......... *A61B 5/0823* (2013.01); *A61B 5/0205* (2013.01); *A61B 5/0816* (2013.01); *A61B 5/7264* (2013.01); *A61B 5/7275* (2013.01); *A61B 7/003* (2013.01); *A61B 7/04* (2013.01)

(58) Field of Classification Search
CPC .... G16H 50/20; A61B 5/0823; A61B 5/0816; A61B 7/003; A61B 2562/0204; A61B 5/7267; A61B 5/08; A61B 5/7264
USPC .......... 600/300, 301, 529, 453, 586; 381/67; 702/188
See application file for complete search history.

(56) References Cited

U.S. PATENT DOCUMENTS

| 5,197,490 | A | * | 3/1993 | Steiner ................. | A61B 5/0017 600/484 |
| 5,309,922 | A | | 5/1994 | Schechter et al. | |
| 6,238,338 | B1 | | 5/2001 | DeLuca et al. | |
| 6,436,057 | B1 | * | 8/2002 | Goldsmith ........... | A61B 5/0806 600/529 |
| 8,121,303 | B2 | | 2/2012 | Tseng et al. | |
| 8,241,223 | B2 | * | 8/2012 | Gavriely ................ | A61B 5/053 327/40 |
| 8,744,087 | B2 | | 6/2014 | Bodley et al. | |
| 8,777,874 | B2 | * | 7/2014 | Zhang .................. | A61B 5/0205 600/484 |
| 9,848,848 | B2 | | 12/2017 | Emmanouilidou et al. | |
| 10,430,946 | B1 | | 10/2019 | Zhou et al. | |
| 10,524,761 | B2 | | 1/2020 | Rajagopal et al. | |
| 2002/0085724 | A1 | | 7/2002 | Grasfield et al. | |
| 2004/0267150 | A1 | * | 12/2004 | Lomask ............... | A61B 5/0823 600/529 |

(Continued)

OTHER PUBLICATIONS

D. Emmanouilidou et al., "Adaptive Noise Suppression of Pediatric Lung Auscultations With Real Applications to Noisy Clinical Settings in Developing Countries," IEEE Transactions on Biomedical Engineering, vol. 62, No. 9, Sep. 2015, pp. 2279-2288.
E.D. McCollum et al., "Digitally Recorded Lung Sounds and Mortality Among Children 1-59 Months Old With Pneumonia in The Pneumonia Etiology Research for Child Health Study," Am J Respir Crit Care Med 2017;195:A1195, pp. 1-2.

(Continued)

*Primary Examiner* — May A Abouelela
(74) *Attorney, Agent, or Firm* — Sterne, Kessler, Goldstein & Fox P.L.L.C.

(57) ABSTRACT

Embodiments disclosed herein improve digital stethoscopes and their application and operation. A first method detects of a respiratory abnormality using a convolution. A second method counts coughs for a patient. A third method predicts a respiratory event based on a detected trend. A fourth method forecasts characteristics of a future respiratory event. In a fifth embodiment, a base station is provided for a digital stethoscope.

17 Claims, 21 Drawing Sheets

(56) References Cited

U.S. PATENT DOCUMENTS

| | | | |
|---|---|---|---|
| 2006/0074334 A1* | 4/2006 | Coyle | A61B 7/003 600/529 |
| 2007/0135691 A1* | 6/2007 | Zingelewicz | G06F 19/3462 600/301 |
| 2008/0232604 A1 | 9/2008 | Dufresne et al. | |
| 2008/0312547 A1* | 12/2008 | Wada | A61B 7/003 600/534 |
| 2009/0082637 A1 | 3/2009 | Galperin | |
| 2009/0216127 A1* | 8/2009 | Gavriely | A61B 5/053 600/453 |
| 2009/0312660 A1* | 12/2009 | Guarino | G10L 17/26 600/529 |
| 2011/0125044 A1 | 5/2011 | Rhee et al. | |
| 2012/0071777 A1* | 3/2012 | MacAuslan | A61B 5/0823 600/529 |
| 2012/0131462 A1* | 5/2012 | Chen | G06F 9/451 715/727 |
| 2012/0302898 A1* | 11/2012 | Zhang | A61B 5/0823 600/484 |
| 2013/0041278 A1 | 2/2013 | Bal et al. | |
| 2013/0131465 A1* | 5/2013 | Yamamoto | A61B 5/7271 600/301 |
| 2013/0316752 A1 | 11/2013 | Bodley et al. | |
| 2014/0012149 A1 | 1/2014 | Trice | |
| 2014/0126732 A1 | 5/2014 | West et al. | |
| 2014/0249378 A1* | 9/2014 | Chan | G06F 19/00 600/301 |
| 2014/0276133 A1 | 9/2014 | Schriefl et al. | |
| 2014/0336537 A1* | 11/2014 | Patel | A61B 7/003 600/586 |
| 2014/0343889 A1 | 11/2014 | Ben Shalom et al. | |
| 2015/0011840 A1* | 1/2015 | Gavriely | A61B 5/0826 600/301 |
| 2015/0023204 A1 | 1/2015 | Wik et al. | |
| 2015/0025417 A1* | 1/2015 | Schmidt | A61B 5/0022 600/586 |
| 2015/0073306 A1* | 3/2015 | Abeyratne | G06K 9/00523 600/586 |
| 2015/0245788 A1* | 9/2015 | Schmidt | G16H 50/20 600/586 |
| 2016/0015359 A1 | 1/2016 | Emmanouilidou et al. | |
| 2016/0100817 A1 | 4/2016 | Hussain | |
| 2016/0262717 A1 | 9/2016 | Smith | |
| 2016/0310068 A1* | 10/2016 | Haviv | A61N 1/36003 |
| 2017/0119303 A1 | 5/2017 | Yadollahi et al. | |
| 2017/0143565 A1* | 5/2017 | Childs | A61G 7/012 |
| 2017/0325717 A1* | 11/2017 | Dellimore | G16H 50/20 |
| 2018/0049716 A1 | 2/2018 | Rajagopal et al. | |
| 2018/0177432 A1 | 6/2018 | Au et al. | |
| 2018/0193259 A1* | 7/2018 | Gerhart | A61K 9/0078 |
| 2018/0242874 A1 | 8/2018 | Johnson et al. | |
| 2018/0248406 A1 | 9/2018 | Bae et al. | |
| 2018/0317876 A1 | 11/2018 | Emmanouilidou et al. | |
| 2019/0083215 A1 | 3/2019 | Serval et al. | |
| 2019/0151585 A1* | 5/2019 | Troxell | A61B 5/7282 |
| 2019/0197414 A1 | 6/2019 | Zerick et al. | |
| 2019/0328278 A1 | 10/2019 | Zabel et al. | |
| 2019/0365342 A1 | 12/2019 | Ghaffarzadegan et al. | |
| 2019/0385073 A1 | 12/2019 | Guo et al. | |
| 2020/0015709 A1* | 1/2020 | Peltonen | A61B 5/0823 |
| 2020/0027558 A1* | 1/2020 | Abeyratne | G16H 50/50 |
| 2020/0107810 A1 | 4/2020 | Hussain | |

OTHER PUBLICATIONS

D. Emmanouilidou et al., "Computerized Lung Sound Screening for Pediatric Auscultation in Noisy Field Environments," IEEE Transactions on Biomedical Engineering, vol. 65, No. 7, Jul. 2018, pp. 1564-1574.

D. Emmanouilidou et al., "Rich Representation Spaces: Benefits in Digital Auscultation Signal Analysis," 2016 IEEE International Workshop on Signal Processing Systems, Dec. 12, 2016, pp. 69-73.

D. Emmanouilidou et al., "A multiresolution analysis for detection of abnormal lung sounds," 34th Annual International Conference of the IEEE EMBS, San Diego, California USA, Aug. 28-Sep. 1, 2012, pp. 3139-3142.

Q.T. Do, A. K. Doig, T. C. Son and J. M. Chaudri, "Personalized Prediction of Asthma Severity and Asthma Attack for Personalized Treatment Regimen," 2018 40th Annual International Conference of the IEEE Engineering in Medicine and Biology Society (EMBC), Honolulu, HI, 2018, pp. 1-5. (Year: 2018).

Chatterjee, Soujanya & Rahman, MD. Mahbubur & Nemanti, Ebrahim & Kuang, Jilong. (2019). WheezeD: Respiration Phase Based Wheeze Detection Using Acoustic Data From Pulmonary Patients Under Attack. 10.4108/eai.20-5-2019.2283516. (Year: 2019).

* cited by examiner

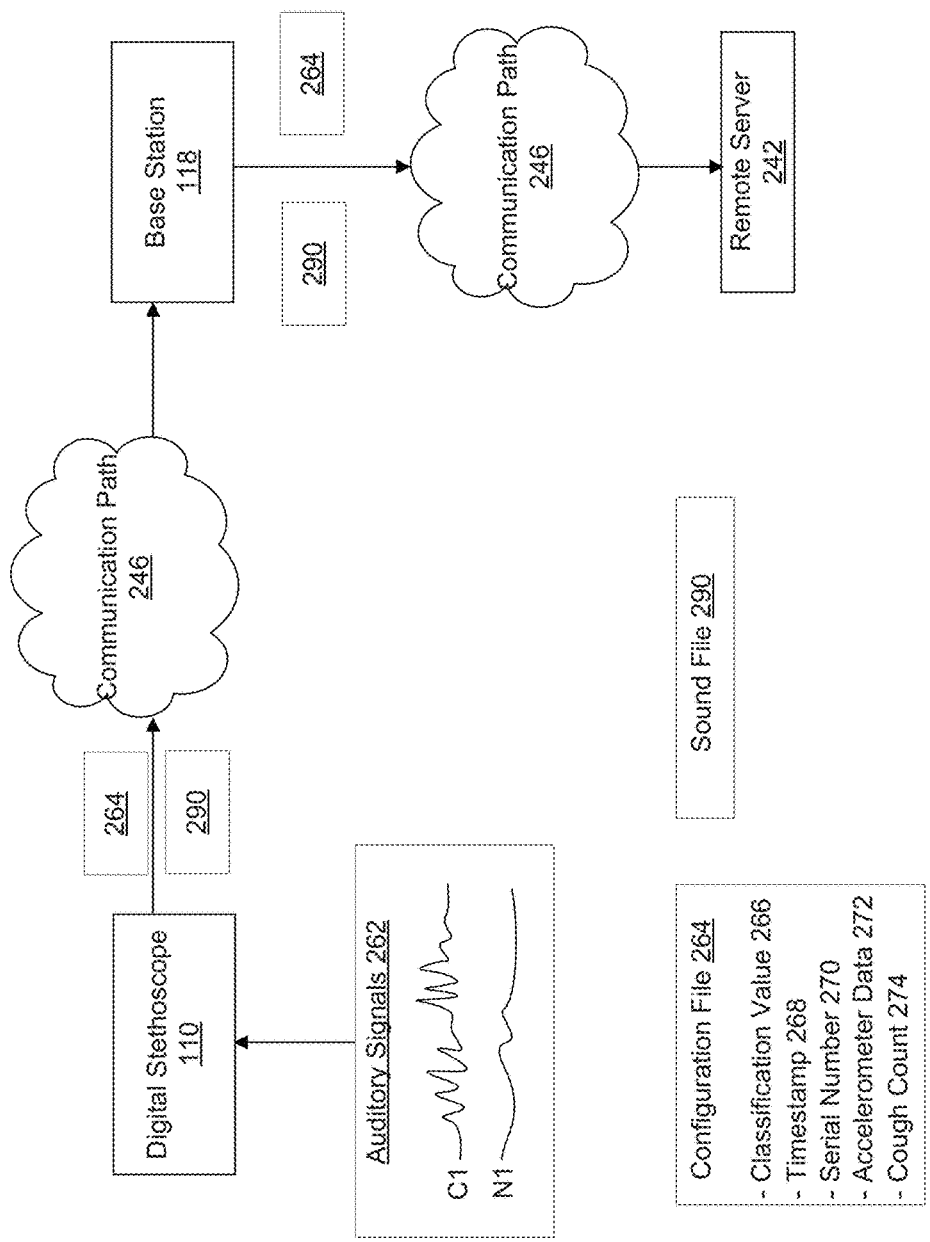

DIGITAL STETHOSCOPE FOR COUNTING COUGHS, AND APPLICATIONS THEREOF

TECHNICAL FIELD

An embodiment relates generally to a digital stethoscope, and more specifically a digital stethoscope for detecting a respiratory abnormality and a method of operation thereof.

BACKGROUND

Respiratory illnesses such as asthma, chronic obstructive pulmonary disease (COPD), bronchitis, emphysema, and pneumonia affect many individuals. The ability to quickly detect and forecast the onset of these conditions, including possible life threatening events associated with these conditions, is of vital importance to those affected. Generally, diagnosis of these respiratory illnesses involves a doctor that listens to patient's breathing using a stethoscope. A stethoscope is an acoustic medical device for auscultation. It typically has a small disc-shaped resonator that is placed against the skin, and a tube connected to two earpieces. However, these traditional stethoscopes are prone to error and require a doctor to be present and to make the diagnosis. The need for a doctor makes daily monitoring for these conditions impractical.

A number of patents and applications have been filed that attempt to deal with these issues. U.S. Pat. No. 9,848,848 describes a digital stethoscope that uses a number of audio filters to control noise and reduce the possibility of error. U.S. Patent Pub. No. 2018/0317876 describes using a classification system, such as a binary support vector machine, to distinguish between those noises that are normal from those that are abnormal.

However, a number of limitations still exist in the art. For example, there is a need to improve real-time performance of the classification algorithm to allow it to be executed in real time and locally on a device that exists at the patient's home. There may be a need to improve the ability to forecast future respiratory future respiratory events. There may be a need to catalog data collected from in-home stethoscopes, while protecting a patient's privacy interest. Currently, a classification system may be able to predict whether a noise is normal or abnormal, but cannot predict a severity of a future respiratory event or the characteristics of that respiratory event. Methods, devices, and systems are needed to address these issues.

SUMMARY

Embodiments disclosed herein improve digital stethoscopes and their application and operation. In a first embodiment, a method detects of a respiratory abnormality using a convolution. The convolution may improve performance, particularly in situations where the detection should occur in real-time. The method involves receiving, from a microphone, an auditory signal. An auditory spectrogram is generated based on the auditory signal. A convolution procedure is performed on the auditory spectrogram to generate one or more convolution values. The convolution values represent a compressed version of a portion of the auditory spectrogram, and the convolution procedure is trained to generate one or more features for detecting the respiratory abnormality. One or more weights trained for detection of the respiratory abnormality are applied to the convolution values. A classification value is generated based on the application of the weights to the convolution values. The classification value indicates whether the auditory signal includes the respiratory abnormality.

In a second embodiment, a method counts coughs for a patient. The method involves receiving from a microphone of a digital stethoscope an auditory signal over a period of time. An auditory spectrogram is generated based on the auditory signal. A control unit of the digital stethoscope analyzes the auditory spectrogram to determine whether the auditory signal represents a cough. The control unit of the digital stethoscope tracks the cough in a cough log. Based on the cough log, a communication unit of the digital stethoscope transmits to a cloud-based service a message indicating a number of coughs tracked over the period of time for storage on a remote server.

In a third embodiment, a method predicts a respiratory event based on a detected trend. The method involves receiving, from a microphone of a digital stethoscope, a first noise signal at a first time. The first noise signal is analyzed to determine a first severity score indicating how severe a first respiratory event of a patient captured in the first noise signal is. A second noise signal captured at a second time is received from the microphone of the digital stethoscope. The second noise signal is analyzed to determine a second severity score indicating how severe a second respiratory event of the patient captured in the second noise signal is. Finally, a prediction is generated indicating a likelihood of a third respiratory event occurring for the patient at a future time based on applying a first weight to the first severity score and a second weight to the second severity score. The first and second weights are trained based on a history of respiratory events.

In a fourth embodiment, a method forecasts characteristics of a future respiratory event. The method involves receiving, from a microphone of a digital stethoscope, a first noise signal. The first noise signal captures a first respiratory event at a first time. A first feature space representing the first noise signal is generated. The first feature space is encoded into a first convolution vector using a convolution procedure. A second noise signal is received, from the microphone of the digital stethoscope. The second noise signal captures a second respiratory event at a second time. A second feature space representing the second noise signal is generated. The second feature space is encoded into a second convolution vector using the convolution procedure. A predicted convolution vector is generated based on the first and second feature spaces. Finally, the predicted convolution vector is decoded into a predicted feature space representing a sound made by the future respiratory event.

In a fifth embodiment, a base station is provided for a digital stethoscope. The base station includes a housing configured to accept the digital stethoscope. The base station includes a wireless charging unit, located within the housing, configured to charge the digital stethoscope when it rests on the exterior of the housing. The wireless charging unit is further configured to detect when the digital stethoscope becomes detached from the housing. A communication unit is coupled to the wireless charging unit. The communication unit is configured to receive a noise signal from the digital stethoscope when the wireless charging unit detects the digital stethoscope becoming detached from the housing and to communicate the respiratory event to a cloud-based service. Finally, a control unit is coupled to the communication unit and is configured to analyze the noise signal for a respiratory event.

Certain embodiments of the invention have other steps or elements in addition to or in place of those mentioned above.

The steps or elements will become apparent to those skilled in the art from a reading of the following detailed description when taken with reference to the accompanying drawings.

BRIEF DESCRIPTION OF THE DRAWINGS

The accompanying drawings, which are incorporated herein and form a part of the specification, illustrate embodiments of the present disclosure and, together with the description, further serve to explain the principles of the disclosure and to enable a person skilled in the arts to make and use the embodiments.

FIG. 2B is an exemplary control flow of the system for detecting the respiratory abnormality in an embodiment of the present invention.

In the drawings, like reference numbers generally indicate identical or similar elements. Additionally, generally, the left-most digit(s) of a reference number identifies the drawing in which the reference number first appears.

DETAILED DESCRIPTION

Digital Stethoscope and Base Station

Figure 1:
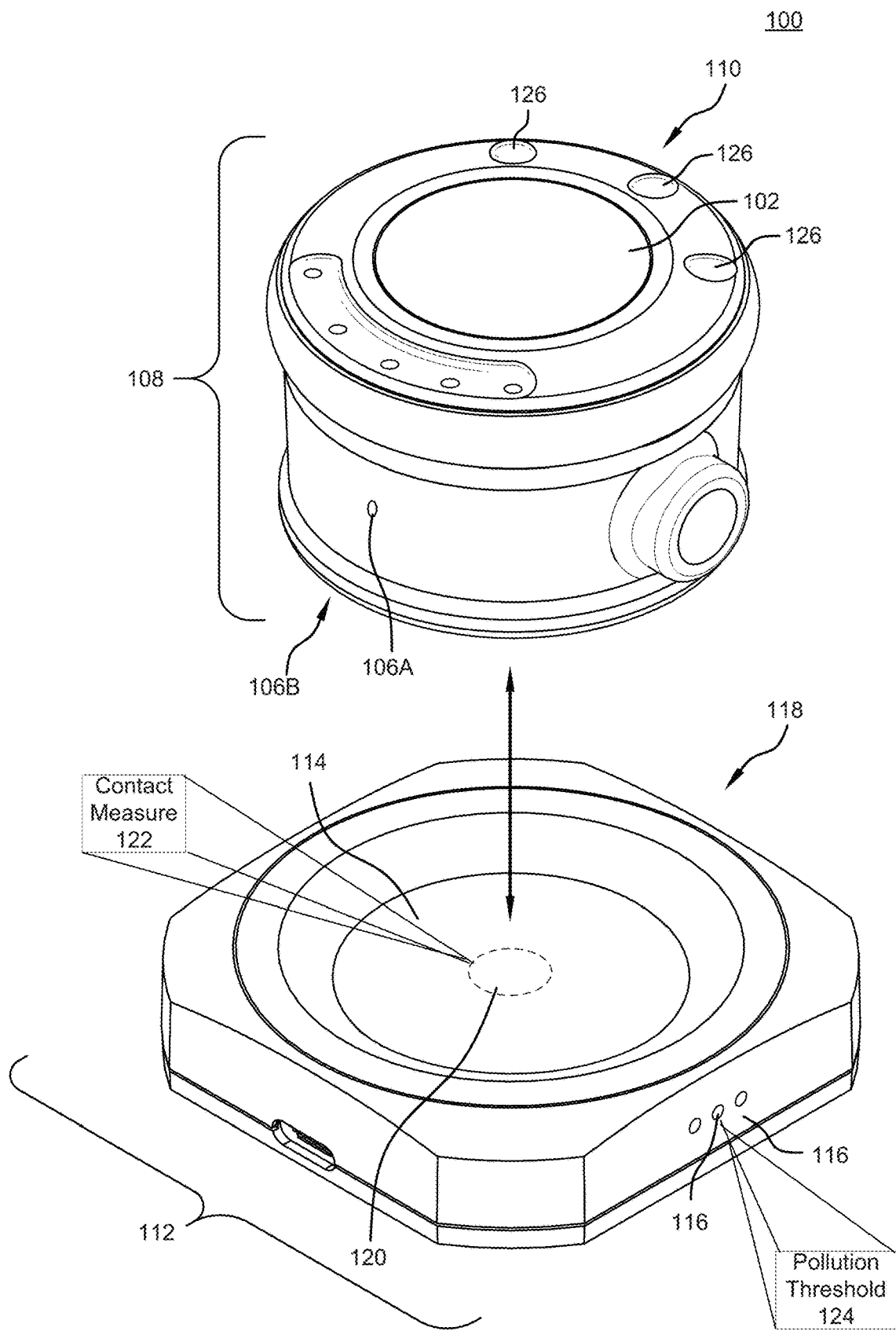
FIG. 1 is an exemplary digital stethoscope and base station of a system for detecting a respiratory abnormality in an embodiment of the present invention.

FIG. 1 shows an exemplary digital stethoscope 110 and base station 118 of a system 100 for detecting a respiratory abnormality in an embodiment of the present invention. The respiratory abnormality refers to irregularities in the respiration patterns of a patient. The respiratory abnormality can indicate the onset of a respiratory condition in a patient, for example a respiratory disease such as asthma, chronic obstructive pulmonary disease (COPD), bronchitis, emphysema, pneumonia, or a combination thereof. The respiratory abnormality can be indicated by the occurrence of a respiratory event, such as a large number of coughs within a period of time by a patient, a wheeze, a crackle, or a cough that has a sound frequency outside an audible frequency expected from a patient, or a combination thereof. The system 100 can use the digital stethoscope 110 and the base station 118 to detect the respiratory abnormality, or predict a respiratory event or respiratory condition in the future.

The digital stethoscope 110 is an acoustic device for detecting and analyzing noises from a patient's body. The patient can be, for example, a human or an animal. The noises, from the patient's body can be for example a cough, a wheeze, a crackle, a breathing pattern, a heartbeat, a chest motion representing a patient's respiratory cycle, or a combination thereof.

The digital stethoscope 110 can further generate information based on the detection, amplification, and analysis of the noises. For example, in one embodiment, the digital stethoscope 110 can generate a value representing or classifying the noises detected.

In one embodiment, the classification can include classifications such as "normal" or "abnormal." "Normal" refers to the classification of sounds falling within an expected frequency range to be heard from the patient. "Abnormal" refers to the classification of sounds falling outside an expected frequency range to be heard from the patient. Classification can be done by analyzing the noises, by for example, filtering, comparing, processing, or a combination thereof, the noises, against threshold values, stored values, acoustic models, machine learned trained data, machine learning processes, or a combination thereof, and putting the noises into categories, for example "normal" or "abnormal" based on the noises being within a range of frequencies expected to be heard from the patient. The collection, filtering, comparison, and classification of the noises by the digital stethoscope 110 will be discussed further below.

The digital stethoscope 110 can include one or more components. For example, in one embodiment, the digital stethoscope 110 can include a display unit 102, one or more microphones 106, and a first housing 108. The display unit 102 can be any graphical user interface such as a display, a projector, a video screen, a touch screen, or any combination thereof that can present information detected or generated by the digital stethoscope 110 for visualization by a user of the system 100. The display unit 102 can enable the visual presentation of information detected or generated by the digital stethoscope 110.

For example, in one embodiment, the display unit 102 can enable the visual presentation of the noises detected, by for example, displaying a plot of the sound frequencies detected over time, displaying a decibel level of the sounds detected, or displaying a value or visual indicator representing the classification of the noises generated, for example "normal" or "abnormal." In one embodiment, if the digital stethoscope 110 classifies a noise as being "abnormal," the display unit 102 can display an indicator, such as a red colored light, or a message indicating that the noise is "abnormal." Alternatively, if the digital stethoscope 110 classifies the noise as being "normal," the display unit 102 can display an indicator, such as a green colored light, or a message indicating that the noise is "normal."

The display unit 102 can further present other information generated by the digital stethoscope 110, such as a power level indicator indicating how much power the digital stethoscope has, a volume indicator indicating the volume level of output noises being output by the digital stethoscope 110, or a network connectivity indicator indicating whether the digital stethoscope 110 is connected to a device or computer network such as a wireless communication network or wired communication network. The aforementioned information are merely exemplary of the types of information that the display unit 102 can display, and are not meant to be limiting.

In one embodiment, the display unit 102 can further include one or more buttons 126 that can be used by the user of the system 100 to enable interaction with the digital stethoscope 110. For example, the buttons 126 can provide functionality such as powering the digital stethoscope 110 on or off or enable the digital stethoscope 110 to start or stop recording the noises.

In one embodiment, the digital stethoscope 110 can further include one or more microphones 106A and B. The microphones 106A and B enable the digital stethoscope 110 to detect and convert the noises into electrical signals for processing by the digital stethoscope 110, or a further device such as the base station 118. Microphone 106A is mounted on a perimeter side of stethoscope 110 to detect noises external to the patient's body. The noises originating from external to the patient's body can be for example background noise, white noise, or a combination thereof. Microphone 106B may be mounted on a side reverse of display 102 and may detect noises originating from the patient's body.

The microphones 106A and B can be standalone devices or can be arranged in an array configuration, where the microphones 106 operate in tandem to detect the noises. In one embodiment, each microphone in the array configuration 104 can serve a different purpose. For example, each microphone in the array configuration 104 can be configured to detect and convert into electrical signals the noises at different frequencies or within different frequency ranges such that each of the microphones 106 can be configured to detect specific noises. The noises detected by the microphones 106 can be used to generate the values for classifying the noises as "normal" or "abnormal," and can be further used to predict the respiratory event or respiratory condition in the future.

The digital stethoscope 110 can further have a first housing 108 enclosing the components of the digital stethoscope 110. The first housing 108 can separate components of the digital stethoscope 110 contained within from other components external to the first housing 108. For example, the first housing 108 can be a case, a chassis, a box, or a console. In one embodiment, for example, the components of the digital stethoscope 110 can be contained within the first housing 108. In another embodiment, some components of the digital stethoscope 110 can be contained within the first housing 108 while other components, such as the display 102, the microphones 106, the buttons 126, or a combination thereof, can be accessible external to the first housing 108. The aforementioned are merely examples of components that can be contained in or on the first housing 108 and are not meant to be limiting. Further discussion of other components of the digital stethoscope 110 will be discussed below.

The system 100 can further include a base station 118. The base station 118 is a special purpose computing device that enables computation and analysis of the noises obtained by the digital stethoscope 110 in order to detect the respiratory abnormality, or to predict the respiratory event or respiratory condition in the future. The base station 118 can provide additional or higher performance processing power compared to the digital stethoscope 110. In one embodiment, the base station 118 can work in conjunction with the digital stethoscope 110 to detect, amplify, adjust, and analyze noises from a patient's body by, for example, providing further processing, storage, or communication capabilities to the digital stethoscope 110. In another embodiment, the base station 118 can work as a standalone device to detect, amplify, adjust, and analyze noises to detect the respiratory abnormality, or to predict the respiratory event or respiratory condition in the future.

The base station 118 can analyze of the noises captured by stethoscope 110. For example, in one embodiment, the base station 118 can generate values classifying the noises detected as "normal" or "abnormal." The collection, filtering, comparison, and classification of the noises by the base station 118 will be discussed further below.

The base station 118 can include one or more components. For example, in one embodiment, the base station 118 can include a charging pad 114, one or more air quality sensors 116, a contact sensor 120, and a second housing 112. The charging pad 114 can enable the electric charging of the digital stethoscope 110, through inductive charging where an electromagnetic field is used to transfer energy between the charging pad 114 and a further device, such as the digital stethoscope 110, using electromagnetic induction.

In one embodiment, the charging pad 114 can enable electric charging of the digital stethoscope 110 upon detecting contact or coupling, via the contact sensor 120, between the digital stethoscope 110 and the charging pad 114. For example, in one embodiment, if the digital stethoscope 110 is coupled to the charging pad 114 by physical placement of the digital stethoscope 110 on the charging pad 114, the contact sensor 120 can detect a weight or an electromagnetic signal produced by the digital stethoscope 110 on the charging pad 114, and upon sensing the weight or the electromagnetic signal enable the induction process to transfer energy between the charging pad 114 and the digital stethoscope 110.

In another embodiment, if the digital stethoscope 110 is coupled to the charging pad 114 by placing the digital stethoscope 110 in proximity of the charging pad 114 without physically placing the digital stethoscope 110 on the charging pad 114, the contact sensor 120 can detect an electric current or a magnetic field from one or more components of the digital stethoscope 110 and enable the induction process to transfer energy between the charging pad 114 and the digital stethoscope 110.

The contact sensor 120 is a device that senses mechanical or electromagnetic contact and gives out signals when it does so. The contact sensor 120 can be, for example, a pressure sensor, a force sensor, strain gauges, piezoresistive/piezoelectric sensors, capacitive sensors, elastoresistive sensors, torque sensors, linear force sensors, an inductor, other tactile sensors, or a combination thereof configured to measure a characteristic associated with contact or coupling between the digital stethoscope 110 and the charging pad 114. Accordingly, the contact sensor 120 can output a contact measure 122 that represents a quantified measure, for example, a measured force, a pressure, an electromagnetic force, or a combination thereof corresponding to the coupling between the digital stethoscope 110 and the charging pad 114. For example, the contact measure 122 can detect one or more force or pressure readings associated with forces applied by the digital stethoscope 110 on the charging pad 114. The contact measure 122 can further detect one or more electric current or magnetic field readings associated with placing the digital stethoscope 110 in proximity of the charging pad 114.

In one embodiment, the base station 118 can further include one or more air quality sensors 116. The air quality sensors 116 are devices that detect and monitor the presence of air pollution in a surrounding area. Air pollution refers to the presence of or introduction into the air of a substance which has harmful or poisonous effects on the patient's body. For example, the air quality sensors 116 can detect the presence of particulate matter or gases such as ozone, carbon monoxide, sulfur dioxide, nitrous oxide, or a combination thereof that can be poisonous to the patient's body, and in particular poisonous to the patient's respiratory system.

In one embodiment, based on the air quality sensors 116 detecting the presence of air pollution, the base station 118 can determine whether the amount of air pollution poses a health risk to the patient by, for example, comparing the levels of air pollution to a pollution threshold 124 to determine whether the levels of air pollution in the surrounding area of the base station 118 pose a health risk to the patient. The pollution threshold 124 refers to a pre-determined level for particulate matter or gases measured in micrograms per cubic meter (m/m3), parts per million (ppm), or parts per billion (ppb), that if exceeded poses a health risk to the patient For example, in one embodiment, if the air quality sensors 116 detect the presence of sulfur dioxide above 75 ppb in the air surrounding the base station 118, the base station 118 can determine that the air pollution in the surrounding area poses a health risk to the patient. The detection of air pollution can further be used for detecting the respiratory abnormality or to predict the respiratory event or respiratory condition in the future in the patient by allowing the system 100 to determine what factors are contributing to the "normal" or "abnormal" classification of the noises, or what factors are contributing to the data detected and generated by the system 100 which can be used to predict a respiratory event or respiratory condition in the future.

The base station 118 can further have a second housing 112 enclosing the components of the base station 118. The second housing 112 can separate components of the base station 118 contained within, from other components external to the second housing 112. For example, the second housing 112 can be a case, a chassis, a box, or a console. In one embodiment, for example, the components of the base station 118 can be contained within the second housing 112.

In another embodiment, some components of the base station 118 can be contained within the second housing 112 while other components, such as the charging pad 114 or the air quality sensors 116 can be accessible external to the second housing 112. The aforementioned are merely examples of components that can be contained in or on the second housing 112 and are not meant to be limiting. Further discussion of other components of the base station 118 will be discussed below.

Figure 1A:
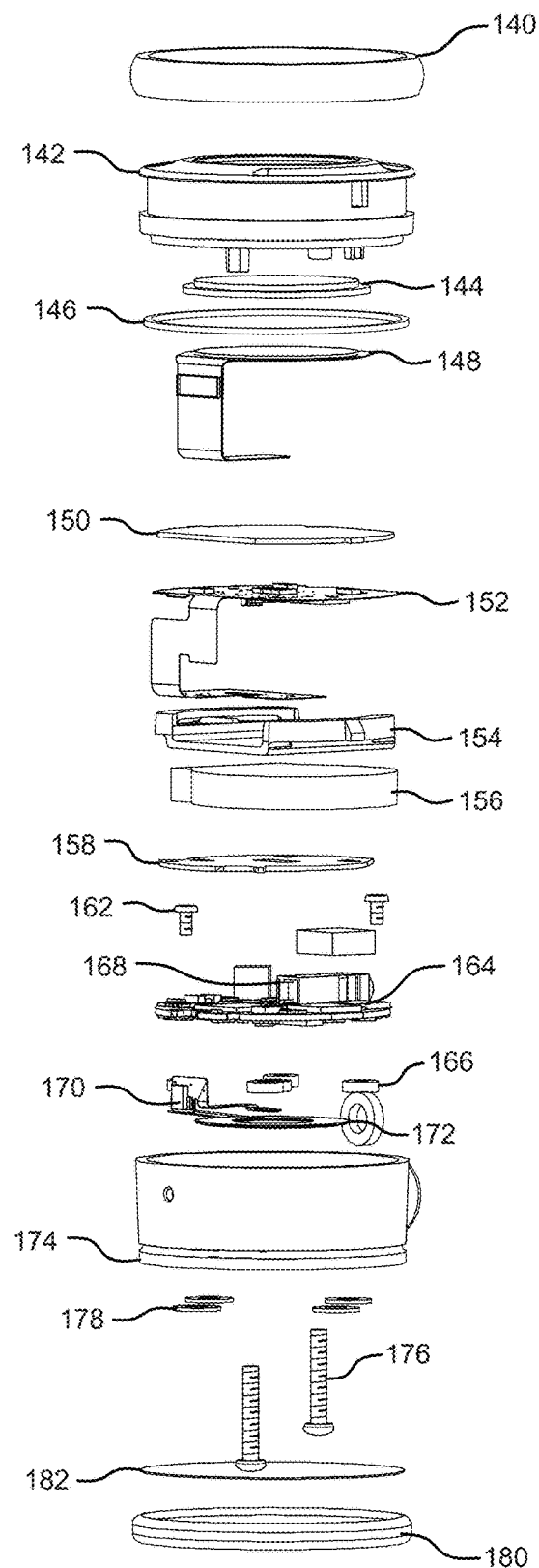
FIG. 1A is an exemplary architecture of the digital stethoscope in an embodiment of the present invention.

Referring now to FIG. 1A, therein is shown an exemplary architecture of the digital stethoscope 110 in an embodiment. In various embodiments, the digital stethoscope 110 can include, alternatively or additionally:

- a grip ring 140 located around a first upper portion 142 of the first housing 108 which provides a gripping surface for a user of the system 100 to hold the digital stethoscope 110;
- a glass lens 144 of the display unit 102, which protects the display components, such as for example liquid crystal displays (LCD) of the display unit 102. The glass lens 144 can sit on top of a housing gasket 146, which stabilizes and holds the glass lens 144;
- a display housing unit 148, on which the housing gasket 146 sits and which contains the components of the display unit 102, such as for example the LCDs;
- a flex backing 150 which on which the display housing 148 sits and which provides stability for the display housing 148;
- a flex assembly 152, on which the flex backing 150 sits and which provides stability for the flex backing 150;
- a retainer clip 154 which holds the flex assembly 152 in place;
- a battery housing 156, to which a battery board 158 can couple, and which can hold battery components of the digital stethoscope 110;
- a first printed circuit board assembly 164, which can hold the circuitry, including any processors, memory components, active and passive components, or a combination thereof, of the digital stethoscope 110;
- one or more first screws 162 that couples the first printed circuit board assembly 164 to the other components of the digital stethoscope 110;
- an audio jack 168 to allow output of noise signals detected by the digital stethoscope 110;
- a microphone assembly 170, on which the microphones 106 can be housed;
- components such as an O-ring 172 and one or more coils 166 that couple the microphone assembly 170 to the first printed circuit board assembly 164.
- a first bottom portion 174 of the first housing 108 on which the microphone assembly 170 sits;
- a diaphragm membrane 182 which forms the bottom surface of the digital stethoscope 110, and which is coupled to the first bottom portion 174 of the first housing 108 with one or more second screws 176 and one or more washers 178; and
- a diaphragm ring 180 coupled to the diaphragm membrane 182, which provides a gripping surface for the first bottom portion 174 of the digital stethoscope 110, such that the digital stethoscope 110 does not slip when placed on a surface.

The aforementioned components are merely exemplary and represent one embodiment of the digital stethoscope 110.

Figure 1B:
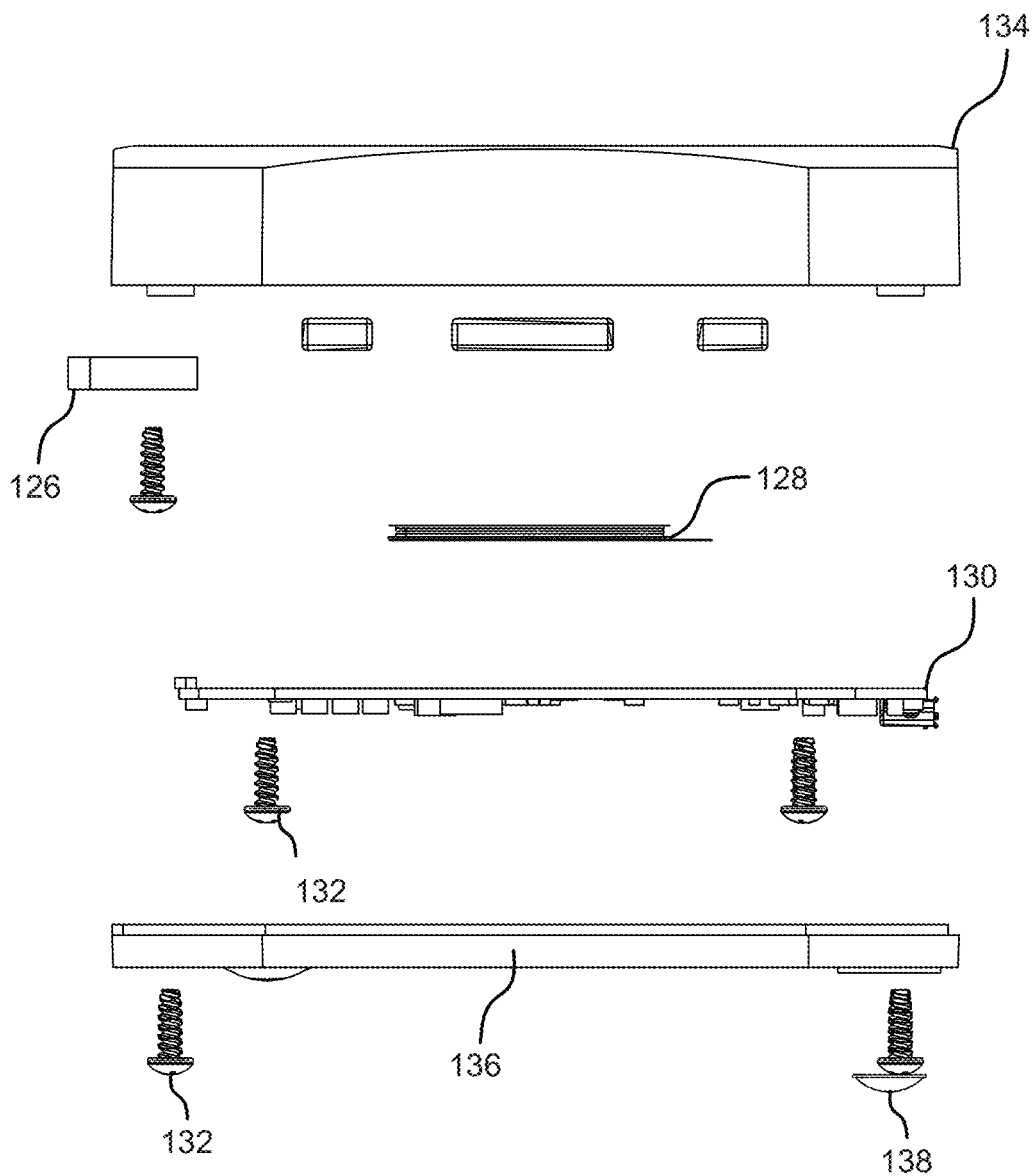
FIG. 1B is an exemplary architecture of the base station in an embodiment of the present invention.

Referring now to FIG. 1B, that figure illustrates an exemplary architecture of the base station 118 in an embodiment of the present invention. In various embodiments, the base station 118 can include, alternatively or additionally:

- a second upper portion 134 of the second housing 112;
- a second printed circuit board assembly 130 which can hold the circuitry, including any processors, memory components, active and passive components, or a combination thereof, of the base station 118;
- one or more third screws 132 that couples the second printed circuit board assembly 130 to the second upper portion 134 of the second housing 112 via one or more second connectors 126;
- one or more coils 128, coupled to the second printed circuit board assembly 130, which can detect the weight or the electromagnetic signal produced by the digital stethoscope 110 on the base station 118;
- a second bottom portion 136 of the second housing 112, which forms the bottom surface of the base station 118; and
- one or more bumpers 138 to cover and protect the third screws 132.

The aforementioned components are merely exemplary and represent one embodiment of the base station 118.

Figure 2A:
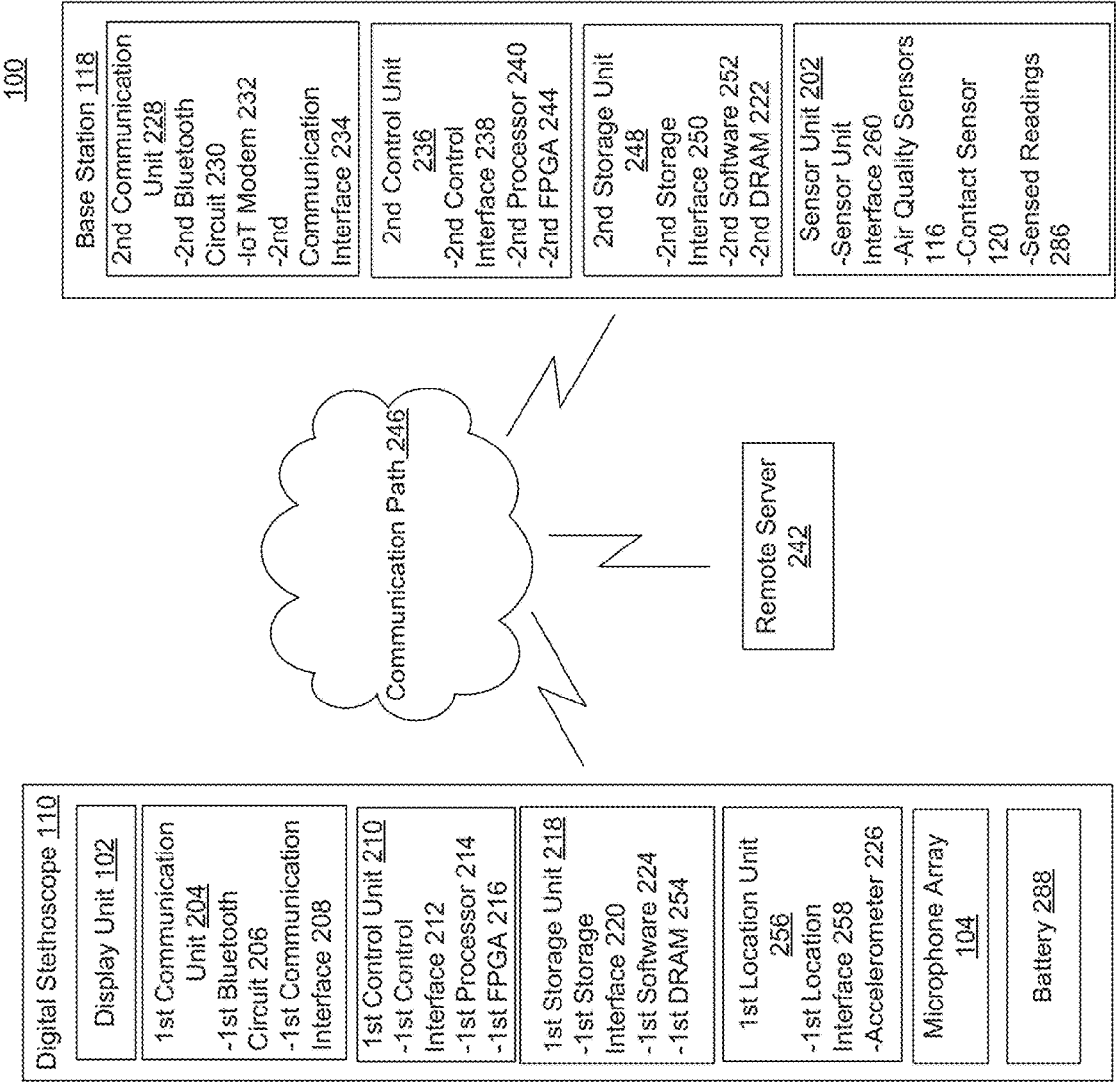
FIG. 2A is a network diagram of the system for detecting the respiratory abnormality including further components of the digital stethoscope and base station in an embodiment of the present invention.

Referring now to FIG. 2A, that figure shows a network diagram of the system 100 for detecting the respiratory abnormality including further components of the digital stethoscope 110 and base station 118 in an embodiment of the present invention. FIG. 2A shows an embodiment where the digital stethoscope 110 is connected to the base station 118 through a device or computer network, such as a wireless or wired network, via a communication path 246. FIG. 2A further shows an embodiment where a remote server 242 is connected to the digital stethoscope 110 and the base station 118 via the communication path 246.

The remote server 242 can provide additional or higher performance processing power compared to the digital stethoscope 110 and the base station 118. In one embodiment, the remote server 242 can work in conjunction with the digital stethoscope 110, the base station 118, or a combination thereof to analyze the detected noises. For example, in one embodiment, the remote server 242 can provide some or all of the processing power of the system 100 to process the information detected or generated by the digital stethoscope 110, the base station 118, or a combination thereof.

In one embodiment, the remote server 242 can further provide additional storage capabilities to the digital stethoscope 110, the base station 118, or a combination thereof by enabling the storage of information detected or generated by the digital stethoscope 110, the base station 118, or a combination thereof, and provide access to the digital stethoscope 110, the base station 118, or a combination thereof of the information for later use. For example, in one embodiment, the remote server 242 can store the noises detected by the digital stethoscope 110, the base station 118, or a combination thereof for later retrieval by the digital stethoscope 110, the base station 118, or a combination thereof.

In one embodiment, the remote server 242 can further provide information, such as the pre-determined threshold values, stored values, acoustic models, machine learned trained data, machine learning processes, configuration data, or a combination thereof to the digital stethoscope 110, the base station 118, or a combination thereof to allow the digital stethoscope 110, the base station 118, or a combination thereof to perform some or all of their functions. For example, the remote server 242 can store and provide access to the pollution threshold 124 to the base station 118 to allow the base station 118 to perform the computations and comparisons needed to detect and monitor the presence of air pollution in the surrounding area.

In one embodiment, the remote server 242 can further provide configuration data, such as software updates, including updated acoustic models, machine learned trained data, machine learning processes, or a combination thereof to the digital stethoscope 110, the base station 118, or a combination thereof to allow the digital stethoscope 110, the base station 118, or a combination thereof to perform computations and analysis in order to determine the classifications of the noises and to detect the respiratory abnormality or to predict the respiratory event or respiratory condition in the future.

The remote server 242 can be any of a variety of centralized or decentralized computing devices. For example, the remote server 242 can be a laptop computer, a desktop computer, grid-computing resources, a virtualized computing resource, cloud computing resources, routers, switches, peer-to-peer distributed computing devices, a server, or a combination thereof. The remote server 242 can be centralized in a single room, distributed across different rooms, distributed across different geographical locations, or embedded within a telecommunications network. The remote server 242 can couple with the communication path 246 to communicate with the digital stethoscope 110, the base station 118, or a combination thereof.

The communication path 246 can span and represent a variety of networks and network topologies. For example, the communication path 246 can include wireless communication, wired communication, optical communication, ultrasonic communication, or a combination thereof. For example, satellite communication, cellular communication, Bluetooth, Infrared Data Association standard (IrDA), wireless fidelity (WiFi), and worldwide interoperability for microwave access (WiMAX) are examples of wireless communication that can be included in the communication path 246. Cable, Ethernet, digital subscriber line (DSL), fiber optic lines, fiber to the home (FTTH), and plain old telephone service (POTS) are examples of wired communication that can be included in the communication path 246. Further, the communication path 246 can traverse a number of network topologies and distances. For example, the communication path 246 can include direct connection, personal area network (PAN), local area network (LAN), metropolitan area network (MAN), wide area network (WAN), or a combination thereof.

Also for illustrative purposes, the system 100 is shown with the digital stethoscope 110, the base station 118, and the remote server 242 as end points of the communication path 246, although it is understood that the system 100 can have a different partition between the digital stethoscope 110, the base station 118, the remote server 242, and the communication path 246. For example, the digital stethoscope 110, the base station 118, and the remote server 242, or a combination thereof can also function as part of the communication path 246.

In one embodiment, the digital stethoscope 110 can include further components including a first control unit 210, a first storage unit 218, a first communication unit 204, the first display unit 102, the microphone array 104, a first location unit 256, and a battery 288. The first control unit 210 can include a first control interface 212. The first control unit 210 can execute a first software 224 to provide the intelligence of the system 100. The first control unit 210 can be implemented in a number of different ways. For example, the first control unit 210 can be a first processor 214, a first field programmable gate array (FPGA) 216, an application specific integrated circuit (ASIC), an embedded processor, a microprocessor, a hardware control logic, a hardware finite state machine (FSM), a digital signal processor (DSP), or a combination thereof.

The first control interface 212 can be used for communication between the first control unit 210 and other components of the digital stethoscope 110. The first control interface 212 can also be used for communication that is external to the digital stethoscope 110. The first control interface 212 can receive information from the other components of the digital stethoscope 110 or from external sources, or can transmit information to the other components of the digital stethoscope 110 or to external destinations. The external sources and the external destinations refer to sources and destinations external to the digital stethoscope 110. The first control interface 212 can be implemented in different ways and can include different implementations depending on which components or external units are being interfaced with the first control interface 212. For example, the first control interface 212 can be implemented with a pressure sensor, an inertial sensor, a microelectromechanical system (MEMS), optical circuitry, waveguides, wireless circuitry, wireline circuitry such as a bus interface, an application programming interface (API), or a combination thereof.

The first storage unit 218 can store the first software 224 to provide the intelligence of the system 100. For illustrative purposes, the first storage unit 218 is shown as a single element, although it is understood that the first storage unit 218 can be a distribution of storage elements. Also for illustrative purposes, the system 100 is shown with the first storage unit 218 as a single hierarchy storage system, although it is understood that the system 100 can have the first storage unit 218 in a different configuration. For example, the first storage unit 218 can be formed with different storage technologies forming a memory hierarchal system including different levels of caching, main memory, rotating media, or off-line storage. The first storage unit 218 can be a volatile memory, a nonvolatile memory, an internal memory, an external memory, or a combination thereof. For example, the first storage unit 218 can be a nonvolatile storage such as non-volatile random access memory (NVRAM), Flash memory, disk storage, or a volatile storage such as static random access memory (SRAM) or a first dynamic random access memory (DRAM) 254.

The first storage unit 218 can include a first storage interface 220. The first storage interface 220 can be used for communication between the first storage unit 218 and other components of the digital stethoscope 110. The first storage interface 220 can also be used for communication that is external to the digital stethoscope 110. The first storage interface 220 can receive information from the other components of the digital stethoscope 110 or from external sources, or can transmit information to the other components or to external destinations. The first storage interface 220 can include different implementations depending on which components or external units are being interfaced with the first storage unit 218. The first storage interface 220 can be implemented with technologies and techniques similar to the implementation of the first control interface 212.

The first communication unit 204 can enable external communication to and from the digital stethoscope 110. For example, the first communication unit 204 can permit the digital stethoscope 110 to communicate with the remote server 242, the base station 118, an attachment, such as a peripheral device, and the communication path 246. The first communication unit 204 can also function as a communication hub allowing the digital stethoscope 110 to function as part of the communication path 246 and not be limited to be an end point or terminal unit to the communication path 246. The first communication unit 204 can include active and passive components, such as microelectronics or an antenna, for interaction with the communication path 246. The first communication unit 204 can further have circuitry, such as a first Bluetooth circuit 206, a wireless fidelity (WiFi) circuit, a Near Field Communication (NFC) circuit, or a combination thereof for interaction with the communication path 246.

The first communication unit 204 can include a first communication interface 208. The first communication interface 208 can be used for communication between the first communication unit 204 and other components of the digital stethoscope 110. The first communication interface 208 can receive information from the other components of the digital stethoscope 110 or from external sources, or can transmit information to the other components or to external destinations. The first communication interface 208 can include different implementations depending on which components are being interfaced with the first communication unit 204. The first communication interface 208 can be implemented with technologies and techniques similar to the implementation of the first control interface 212. The first communication unit 204 can couple with the communication path 246 to send information to the remote server 242, the base station 118, or a combination thereof.

The first location unit 256 can generate location information, current heading, and current speed and acceleration of the digital stethoscope 110, as examples. The first location unit 256 can be implemented in many ways. For example, the first location unit 256 can include components, such as a GPS receiver, an inertial navigation system, a cellular-tower location system, a pressure location system, an accelerometer 226, a gyroscope, or any combination thereof. The components can be used in conjunction with other components of the digital stethoscope 110 to detect movements or the location of the patient. For example, in one embodiment, the accelerometer 226 can be used to detect whether the patient or a portion of the patient's body is moving, for example to detect a chest motion representing a patient's respiratory cycle. For example, if the digital stethoscope 110 is placed on the patient's chest, the accelerometer 226 can detect the up and down movement of the patient's chest to determine the frequency and speed at which the patient's chest is moving. In one embodiment, the location unit 256 can further be used to detect the physical location of the digital stethoscope 110, such as the geographic location. For example, the location unit 256 can detect the location of the digital stethoscope 110 by using the accelerometer 226 in conjunction with the other components, and determine that a patient may be physically moving from one geographic location to another.

In one embodiment, the detection of the movement can generate information and data regarding the noises detected by the digital stethoscope 110. For example, if rapid movement of the digital stethoscope 110 is detected and the digital stethoscope 110 detects high frequency noises at the same time, the digital stethoscope 110 can determine that there is high likelihood that the patient may be moving excessively and can further determine that some of the noise generated by the movement should be removed or filtered because it constitutes unwanted background noise. The information detected as a result of the movement can further be used by the digital stethoscope 110 to adjust and analyze the noises, by for example using the information to amplify certain frequencies of the noises that are desired or necessary for the detection of the respiratory abnormality or to reduce or suppress certain frequencies of the noises that are unwanted and not necessary for the detection of the respiratory abnormality. As a result, the digital stethoscope 110 can reduce noise and amplify the noises to further improve the accuracy when detecting the respiratory abnormality, or to predict a respiratory event or respiratory condition at a future time.

The first location unit 256 can include a first location interface 258. The first location interface 258 can be used for communication between the first location unit 256 and other components of the digital stethoscope 110. The first location interface 258 can also be used for communication that is external to the digital stethoscope 110. The first location interface 258 can be implemented with technologies and techniques similar to the implementation of the first control interface 212.

The battery 288 is the power source for the digital stethoscope 110. In one embodiment, the battery 288 can include one or more electrochemical cells with external connections provided to power the digital stethoscope 110. The electrochemical cells can include primary or non-rechargeable cells, secondary or rechargeable cells, or a combination thereof. For example, in one embodiment, the electrochemical cells can include secondary cells that can be charged wirelessly using electromagnetic induction. In one embodiment, electrochemical cells can include primary cells such as alkaline batteries, lithium batteries, or a combination thereof.

In one embodiment, the base station 118 can include further components including a second control unit 236, a second storage unit 248, a second communication unit 228, and sensor unit 202. The second control unit 236 can include a second control interface 238. The second control unit 236 can execute a second software 252 to provide the intelligence of the system 100. The second software 252 can operate independently or in conjunction with the first software 224. The second control unit 236 can provide additional performance compared to the first control unit 210. The second control unit 236 can be a second processor 240, a second field programmable gate array (FPGA) 244, an application specific integrated circuit (ASIC), an embedded processor, a microprocessor, a hardware control logic, a hardware finite state machine (FSM), a digital signal processor (DSP), or a combination thereof.

The second control unit 236 can include a second control interface 238. The second control interface 238 can be used for communication between the second control unit 236 and other components of the base station 118. The second control interface 238 can also be used for communication that is external to the base station 118. The second control interface 238 can receive information from the other components of the base station 118 or from external sources, or can transmit information to the other components of the base station 118 or to external destinations. The external sources and the external destinations refer to sources and destinations external to the base station 118. The second control interface 238 can be implemented in different ways and can include different implementations depending on which components or external units are being interfaced with the second control interface 238. For example, the second control interface 238 can be implemented with a pressure sensor, an inertial sensor, a microelectromechanical system (MEMS), optical circuitry, waveguides, wireless circuitry, wireline circuitry such as a bus interface, an application programming interface (API), or a combination thereof.

The second storage unit 248 can be sized to provide additional storage capacity to supplement the first storage unit 218. For illustrative purposes, the second storage unit 248 is shown as a single element, although it is understood that the second storage unit 248 can be a distribution of storage elements. Also for illustrative purposes, the system 100 is shown with the second storage unit 248 as a single hierarchy storage system, although it is understood that the system 100 can have the second storage unit 248 in a different configuration. For example, the second storage unit 248 can be formed with different storage technologies forming a memory hierarchal system including different levels of caching, main memory, rotating media, or off-line storage. The second storage unit 248 can be a volatile memory, a nonvolatile memory, an internal memory, an external memory, or a combination thereof. For example, the second storage unit 248 can be a nonvolatile storage such as non-volatile random access memory (NVRAM), Flash memory, disk storage, or a volatile storage such as static random access memory (SRAM) or a second dynamic random access memory (DRAM) 222.

The second storage unit 248 can include a second storage interface 250. The second storage interface 250 can be used for communication between the second storage unit 248 and other components of the base station 118. The second storage interface 250 can also be used for communication that is external to the base station 118. The second storage interface 250 can receive information from the other components of the base station 118 or from external sources, or can transmit information to the other components or to external destinations. The second storage interface 250 can include different implementations depending on which components or external units are being interfaced with the second storage unit 248. The second storage interface 250 can be implemented with technologies and techniques similar to the implementation of the second control interface 238.

The second communication unit 228 can enable external communication to and from the base station 118. For example, the second communication unit 228 can permit the base station 118 to communicate with the digital stethoscope 110, the remote server 242, an attachment, such as a peripheral device, and the communication path 246. The second communication unit 228 can also function as a communication hub allowing the base station 118 to function as part of the communication path 246 and not be limited to be an end point or terminal unit to the communication path 246. The second communication unit 228 can include active and passive components, such as microelectronics or an antenna, for interaction with the communication path 246. The second communication unit 228 can further have circuitry, such as a second Bluetooth circuit 230, a wireless fidelity (WiFi) circuit, a Near Field Communication (NFC) circuit, an internet-of-things (IoT) modem 232, or a combination thereof for interaction with the communication path 246.

The second communication unit 228 can include a second communication interface 234. The second communication interface 234 can be used for communication between the second communication unit 228 and other components of the base station 118. The second communication interface 234 can receive information from the other components of the base station 118 or from external sources, or can transmit information to the other components or to external destinations. The second communication interface 234 can include different implementations depending on which components are being interfaced with the second communication unit 228. The second communication interface 234 can be implemented with technologies and techniques similar to the implementation of the second control interface 238.

The sensor unit 202 can enable the base station 118 to obtain one or more sensed readings 286 used to perform one or more of the base station's 118 functions. The sensed readings 286 can include information or data obtained by the sensor unit 202, the purpose of which is to detect events or changes in the environment of the base station 118 and to send the information to components of the base station 118, the digital stethoscope 110, the remote server 242, external devices such as a peripheral device, or a combination thereof to facilitate the functionality of the system 100. The sensed readings 286 can include the contact measure 122 or the amount of air pollution in the surrounding area. In one embodiment, the sensor unit 202 can include the air quality sensors 116, the contact sensor 120, or a combination thereof.

The sensor unit 202 can include a sensor unit interface 260. The sensor unit interface 260 can be used for communication between the sensor unit 202 and other components of the base station 118. The sensor unit interface 260 can also be used for communication that is external to the base station 118. The sensor unit interface 260 can receive information from the other components of the base station 118 or from external sources, or can transmit information to the other components of the base station 118 or to external destinations. The sensor unit interface 260 can include different implementations depending on which components of the base station 118 or external units are being interfaced with the sensor unit 202. The sensor unit interface 260 can be implemented with technologies and techniques similar to the implementation of the second control interface 238.

Referring now to FIG. 2B, that figure shows an exemplary control flow 200 of the system 100 for detecting the respiratory abnormality in an embodiment. In one embodiment, one or more auditory signals 262 can be detected by the digital stethoscope 110 using the microphones 106. The auditory signals 262 can include the noises from the patient's body or from external to the patient's body. By way of example, FIG. 2B depicts two auditory signals 262, where "C1" represents a cough, crackle, or wheeze originating from the patient's body and "N1" represents a noise signal resulting from noises generated external to the patient's body, for example background noise from a patient's environment. In one embodiment, the auditory signals 262 can be saved in a sound file 290, such as a .wav file generated by the digital stethoscope 110. In one embodiment, once the auditory signals 262 are detected and saved in the sound file 290, the digital stethoscope 110 can amplify, adjust, and analyze the auditory signals 262 in the sound file 290, by for example, subtracting, suppressing, or filtering N1 to leave only C1. In one embodiment, the sound file 290 can be stored on the first storage unit 218, the second storage unit 248, or the remote server 242.

In one embodiment, the digital stethoscope 110, the base station 118, or a combination thereof can further generate a configuration file 264 and store the information from detecting, amplifying, adjusting, and analyzing the auditory signals 262 in the configuration file 264. The configuration file 264 is a computer file, such as a text file, that contains the information from detecting, amplifying, adjusting, and analyzing the auditory signals 262. In one embodiment, the configuration file 264 can be stored in and accessed from the first storage unit 218, the second storage unit 248, or the remote server 242. In one embodiment, the configuration file 264 can include information such as a classification value 266 indicating whether the auditory signals 262 indicate a respiratory sound, noise, or auditory tone that is classified as "normal" or "abnormal." The configuration file 264 can further include a timestamp 268 indicating when the auditory signals 262 were detected, an accelerometer data 272 obtained from the accelerometer 226 indicating movement of the patient, a cough count 274 indicating the number of coughs detected by the digital stethoscope 110 over a period of time, or a combination thereof.

In one embodiment, the configuration file 264 can further include information about devices of the system 100, such as a serial number 270 of the digital stethoscope 110 to indicate what device detected the auditory signals 262. The aforementioned are merely exemplary and other information detected and generated by the digital stethoscope 110 can be stored in the configuration file 264.

In one embodiment, the configuration file 264 can be sent to one or more devices of the system 100. For example, the configuration file 264 can be sent to the digital stethoscope 110, the base station 118, the remote server 242, or a combination thereof to be used in performing adjustments or analysis of the auditory signals 262, or to detect a respiratory abnormality or to predict a respiratory event or respiratory condition in the future. For example, in one embodiment where the digital stethoscope 110, the base station 118, the remote server 242, or a combination thereof are performing some or all of the processing of the auditory signals 262, the digital stethoscope 110, the base station 118, the remote server 242, or a combination thereof can receive the auditory signals 262 via the sound file 290, and further information via the configuration file 264, parse the two files, extract information from the two files, and perform processing based on the information contained in the two files.

Figure 2C:
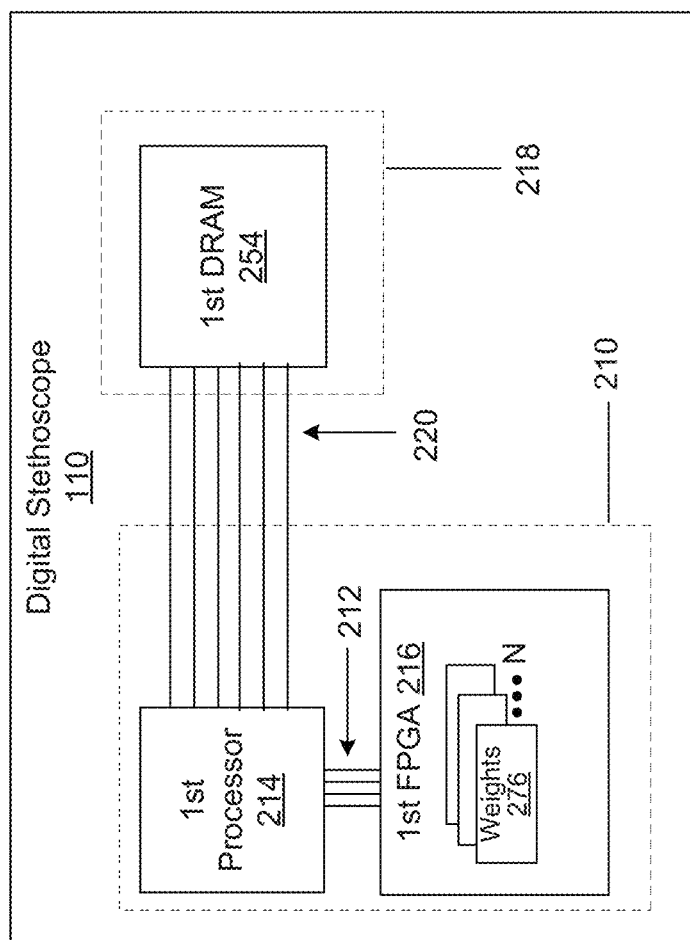
FIG. 2C is a further exemplary architecture of the digital stethoscope in an embodiment of the present invention.

Referring now to FIG. 2C, therein is shown a further exemplary architecture of the digital stethoscope 110 in an embodiment of the present invention. FIG. 2C shows an embodiment where the digital stethoscope 110 includes the first control unit 210 and the first storage unit 218. The first control unit 210 can include the first processor 214 and the first FPGA 216. The first storage unit 218 can include the first DRAM 254. The first processor 214 and the first FPGA 216 can be coupled using the first control interface 212. The first storage unit 218 can be coupled to the first control unit 210 using the first storage interface 220. For example, in one embodiment, the first DRAM 254 can be coupled, via the first storage interface 220 to the first processor 214.

In one embodiment, the first processor 214, the first FPGA 216, and the first DRAM 254 can work in conjunction to process the auditory signals 262 detected by the microphones 106 or the array configuration 104. In one embodiment, the first processor 214 can act as a controller and control the coordination, communications, scheduling, and transfers of data between the first FPGA 216, the first DRAM 254, or other components of the digital stethoscope 110. For example, in one embodiment, the first processor 214 can receive the auditory signals 262 from the microphones 106, and transfer the auditory signals 262 to the first FPGA 216 for further processing. In one embodiment, once the first FPGA 216 has completed its operations, the first FPGA 216 can transfer the output or data generated as a result of its operations back to the first processor 214, which can further transfer the output or data to the first DRAM 254 for storage. In one embodiment, the first processor 214 can further enable the generation of the configuration file 264. In one embodiment, the first processor 214 can further enable the generation of the sound file 290.

In one embodiment, the first FPGA 216 can perform the processing of the auditory signals 262. The first FPGA 216 can include one or more logic blocks, including one or more reconfigurable logic gates, that can be pre-programmed or configured to perform calculations or computations on the auditory signals 262, and to generate output or data to detect the respiratory abnormality, or to predict a respiratory event or respiratory condition in the future. The first FPGA 216 can, for example, have its logic blocks preconfigured with threshold values, stored values, acoustic models, machine learned trained data, machine learning processes, configuration data, or a combination thereof that can be used to perform the processing on the auditory signals 262, the result of which is to detect the respiratory abnormality, or to predict the respiratory event or respiratory condition in the future.

For example, in one embodiment the first FPGA 216 can be preconfigured with a machine learning process, for example a convolutional neural network model, which can have one or more weights 276 associated therewith. The weights 276 refer to values, parameters, thresholds, or a combination thereof that act as filters in the machine learning process and represent particular features of the sounds, noises, and acoustic tones of a respiratory abnormality, respiratory event, respiratory condition, or a combination thereof. The weights 276 can be iteratively adjusted based on machine learned trained data.

Continuing with the example, the first FPGA 216 can, in one embodiment, use the machine learning process, including the weights 276 to detect whether the auditory signals 262 contain a sound, noise, or acoustic tone indicative of a respiratory abnormality, or whether the auditory signals 262 are indicative of a respiratory event or respiratory condition in the future. Further discussion of the processing done by the first FPGA 216 will be discussed below.

Figure 2D:
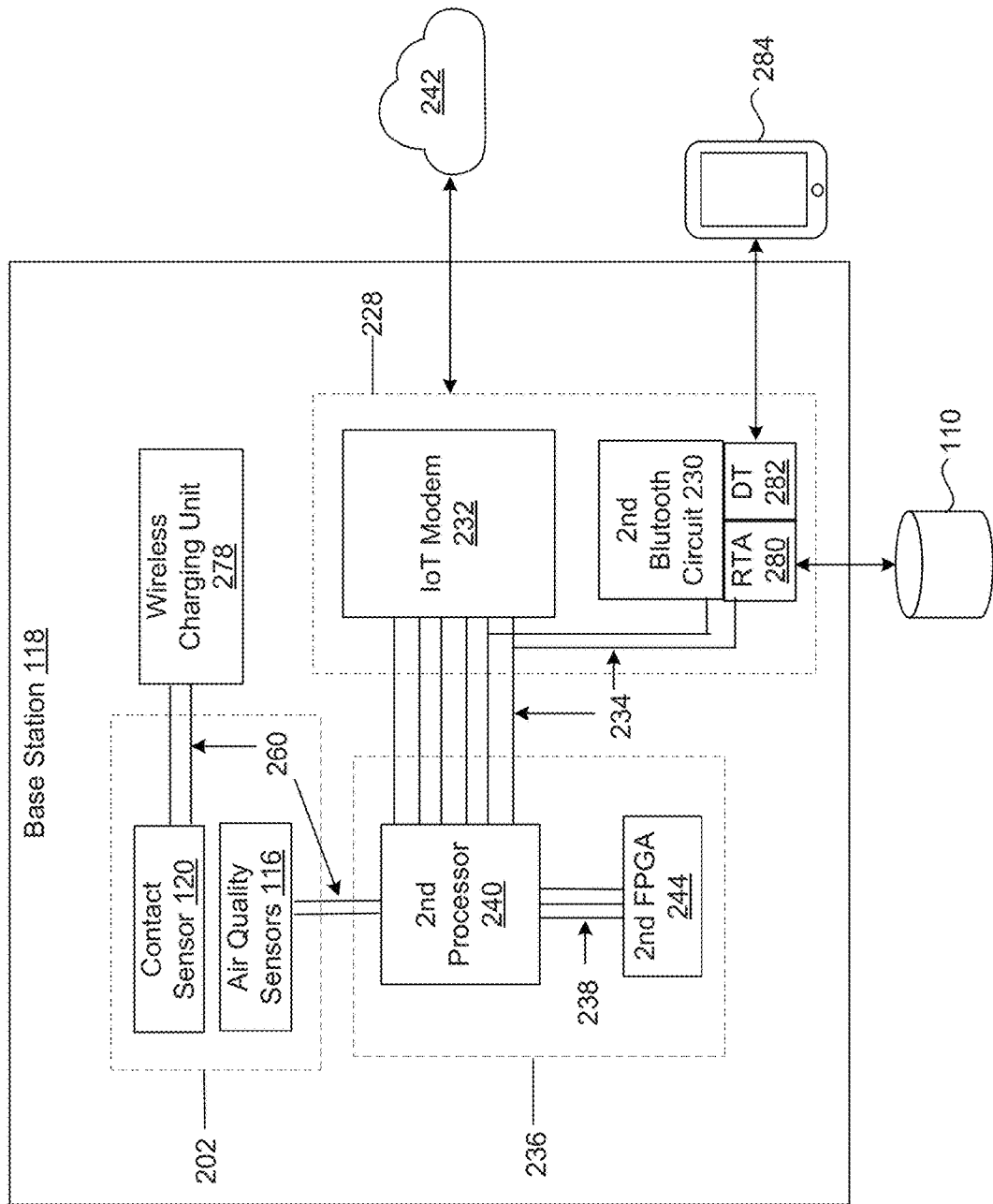
FIG. 2D is a further exemplary architecture of the base station in an embodiment of the present invention.

Referring now to FIG. 2D, therein is shown a further exemplary architecture of the base station 118 in an embodiment of the present invention. FIG. 2D shows an embodiment where the base station 118 includes the second control unit 236, the sensor unit 202, the second communication unit 228, and a wireless charging unit 278. The second control unit 236 can include the second processor 240 and the second FPGA 244. The sensor unit 202 can include the contact sensor 120 and the air quality sensors 116. The second communication unit 228 can include the IoT modem 232 and the second Bluetooth circuit 230. The second Bluetooth circuit 230 can further include a real time audio circuit 280 and a data transfer circuit 282. The real time audio circuit 280 and the data transfer circuit 282 can enable the base station 118 to connect to multiple devices simultaneously over a Bluetooth connection. For example, in one embodiment, the real time audio circuit 280 can enable a Bluetooth connection to the digital stethoscope 110 to send or receive the auditory signals 262 or the sound file 290 containing the auditory signals 262, and the data transfer circuit 282 can enable simultaneous Bluetooth connection to a further device, such as a mobile phone 284 to communicate outputs or data generated by the base station 118 as a result of processing the auditory signals 262. In one embodiment, the IoT modem 232 can further be used to communicate outputs or data generated by the base station 118 to a further device, for example the remote server 242. In one embodiment, the IoT modem 232 can further be used to receive configuration data, such as software updates, including updated acoustic models, machine learned trained data, machine learning processes, firmware, or a combination thereof from the remote server 242. In one embodiment, the base station 118 can further communicate the software updates to the digital stethoscope 110 using the second Bluetooth circuit 230.

The second processor 240 and the second FPGA 244 can be coupled using the second control interface 238. The second communication unit 228 can couple to the second control unit 236 using the second communication interface 234. The sensor unit 202 can couple to the second control unit 236 using the sensor unit interface 260. The sensor unit 202 can couple to the wireless charging unit 278 using the sensor unit interface 260.

In one embodiment, the second processor 240 can act as a controller and control the coordination, communications, scheduling, and transfers of data between the second FPGA 244 and other components of the base station 118. For example, in one embodiment, the second processor 240 can receive the auditory signals 262 from the digital stethoscope 110 via the second communication unit 228, and transfer the auditory signals 262 to the second FPGA 244 for further processing. In one embodiment, once the second FPGA 244 has completed its operations, the second FPGA 244 can transfer the output or data generated as a result of its operations back to the second processor 240, which can further transfer the output or data to other components of the base station 118. For example, the second processor 240 can further transfer the output or data to the second communication unit 228 for transfer to the remote server 242, the mobile device 284, the digital stethoscope 110, or a combination thereof. The mobile device 284 can be a device associated with a user of the system 100 that the base station 118 can use to communicate the output or data generated by the base station 118, the digital stethoscope 110, the remote server 242, or a combination thereof to a user of the system 100. The mobile device 284 can be, for example, a mobile phone, a smart phone, a tablet, a laptop, or a combination thereof.

In one embodiment, the second processor 240 can further generate the configuration file 264 and store values, variables, configuration data, time stamps, or data detected or generated therein. In one embodiment, the second processor 240 can further generate the sound file 290 for storing the auditory signals 262.

In one embodiment, the second FPGA 244 can perform the processing of the auditory signals 262. The second FPGA 244 can include one or more logic blocks, including one or more reconfigurable logic gates, that can be pre-programmed or configured to perform calculations or computations on the auditory signals 262, and to generate output or data generated to detect the respiratory abnormality, or to predict a respiratory event or respiratory condition in the future. The second FPGA 244 can, for example, have its logic blocks preconfigured with threshold values, stored values, acoustic models, machine learned trained data, machine learning processes, configuration data, or a combination thereof that can be used to perform the processing on the auditory signals 262, the result of which is to detect the respiratory abnormality, or to predict the respiratory event or respiratory condition in the future.

For example, in one embodiment the second FPGA 244 can be preconfigured with a machine learning process, for example a convolutional neural network model, which can have one or more weights 276 as shown in FIG. 2C, associated therewith. In another embodiment, the second FPGA 244 can be preconfigured with a machine learning process, for example a long short term memory (LSTM) network model, which can have one or more weights 276 associated therewith. In one embodiment, the second FPGA 244 can be work with the remote server 242 to implement the machine learning process, for example the convolutional neural network model, or the LSTM network model, wherein the second FPGA 244 and the remote server 242 can divide the processing needed to perform the computations done by the machine learning process.

Continuing with the example, the second FPGA 244 can, in one embodiment, use the machine learning process to detect whether the auditory signals 262 contain a sound, noise, or acoustic tone indicative of a respiratory abnormality. In another embodiment, the second FPGA 244 can use the machine learning process to predict a respiratory event or respiratory condition in the future using the auditory signals 262. Further discussion of the processing done by the second FPGA 244 will be discussed below.

The wireless charging unit 278 can enable the electric charging of the digital stethoscope 110, through inductive charging by, for example, generating the electromagnetic field used to transfer energy between the charging pad 114 of FIG. 1, and a further device, such as the digital stethoscope 110 using electromagnetic induction. The wireless charging unit 278 can include the processors, active and passive components, circuitry, control logic, or a combination thereof to enable the inductive charging. In one embodiment, the wireless charging unit 278 can couple to the contact sensor 120 to enable the inductive charging. For example, in one embodiment, if the contact sensor 120 detects contact or coupling between the digital stethoscope 110 and the charging pad 114, the contact sensor 120 can generate the contact measure 122 of FIG. 1, which can be sent to the wireless charging unit 278. The wireless charging unit 278 upon receiving the contact measure 122 can determine that a coupling between the digital stethoscope 110 and the charging pad 114 has occurred and can activate the base station's 118 processors, active and passive components, circuitry, control logic, or a combination thereof to generate the electromagnetic field and begin transferring energy between the charging pad 114 and the digital stethoscope 110. In one embodiment, the wireless charging unit 278 can further power off the base station 118 during the time period in which it is charging the digital stethoscope 110 by, for example, generating a signal to the second processor 240 that charging is taking place and that the components of the base station 118 should be in an off or idle mode during the time period.

In one embodiment, the wireless charging unit 278 can further enable the activation of the base station 118 based on determining a termination of the coupling between the digital stethoscope 110 and the charging pad 114. For example, in one embodiment, the wireless charging unit 278 can detect a termination of the coupling between the digital stethoscope 110 and the charging pad 114 based on a change in the contact measure 122. For example, in one embodiment, if the digital stethoscope 110 is removed from the charging pad 114, the contact sensor 120 can generate a contact measure 122 indicating the removal, and can send the contact measure 122 to the wireless charging unit 278. The wireless charging unit 278 upon receiving the contact measure 122 can determine that the coupling between the digital stethoscope 110 and the charging pad 114 is no longer present and can send a signal to the second processor 240 to activate or power up the components of the base station 118, so that the base station 118 can perform computations and processing on auditory signals 262, or communicate with further devices such as the digital stethoscope 110, the mobile device 284, the remote server 242, or a combination thereof.

Convolutional Neural Network to Detect Abnormality

Figure 3:
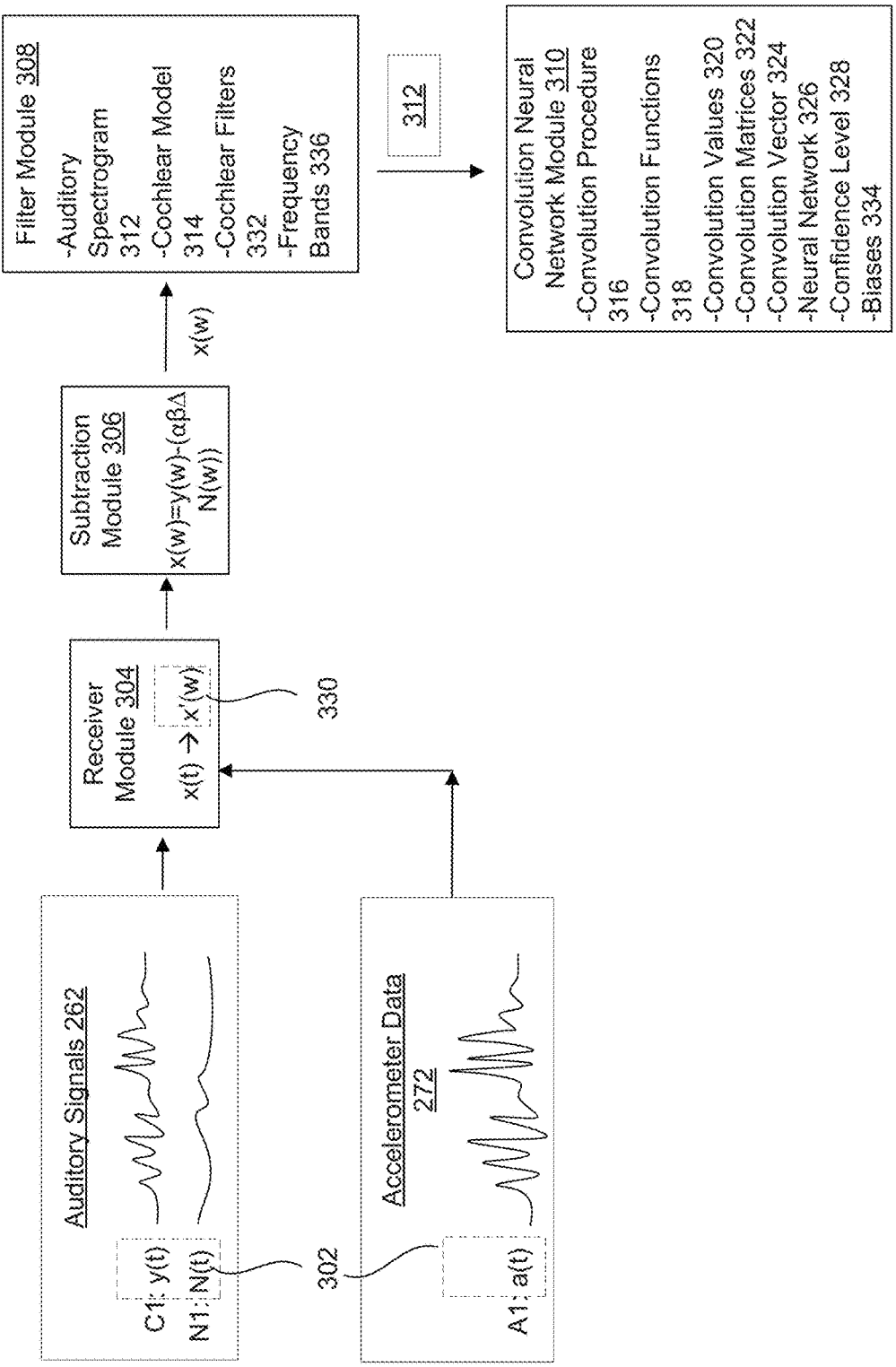
FIG. 3 is an exemplary second control flow for detection of the respiratory abnormality in an embodiment of the present invention.

Referring now to FIG. 3, therein is shown an exemplary second control flow 300 for detection of the respiratory abnormality in an embodiment of the present invention. For brevity of description, in this embodiment, the second control flow 300 will be described as being performed using the digital stethoscope 110. This description is merely exemplary and not meant to be limiting. In other embodiments, the second control flow 300 can be performed using the base station 118, the remote server 242, or a combination thereof.

In one embodiment, the second control flow 300 can be implemented with modules and sub-modules, the components of the digital stethoscope 110, or a combination thereof. In one embodiment, the second control flow 300 can include a receiver module 304, a subtraction module 306, a filter module 308, and a convolution neural network module 310. In one embodiment, the receiver module 304 can couple to the subtraction module 306. The subtraction module 306 can couple to the filter module 308. The filter module 308 can couple to the convolution neural network module 310.

The receiver module 304 can enable receiving of one or more signals or data by the digital stethoscope 110. In one embodiment, the signals or data can be, for example, the auditory signals 262, the accelerometer data 272, or a combination thereof, and can be received via the microphones 106 of FIG. 1, the accelerometer of FIG. 2A, the configuration file 264, the sound file 290, or a combination thereof. By way of example, FIG. 3 depicts two auditory signals 262, where "C1" represents a cough, crackle, or wheeze originating from the patient's body and "N1" represents a noise signal resulting from noises generated external to the patient's body, for example background noise from a patient's environment. FIG. 3 further depicts the accelerometer data 272, where "A1" represents the accelerometer data 272. In one embodiment, C1, N1, and A1, represent time series signals and data, in which the signals are measured over a period of time and can be represented mathematically by one or more time functions 302, in which the value of the time functions 302 vary based on time.

In one embodiment, the receiver module 304 can further enable the conversion of the time functions 302 into one or more frequency domain functions 330, in which the time functions 302 can be represented with respect to a frequency component of the signals or data. The frequency domain functions 330 can be used by the digital stethoscope 118 to perform further calculations or processing of the auditory signals 262, the accelerometer data 272, or a combination thereof to detect the respiratory abnormality. For example, in one embodiment, C1 and N1 can be represented as a combined time function 302 x(t), where x(t) can be represented by equation (1) below:

$$x(t)=y(t)+N(t) \quad (1)$$

In equation (1), y(t) represents the time function 302 of C1 and N(t) represents the time function 302 of N1. The receiver module 304 can convert x(t) into a frequency domain function 330 by, for example, performing a Fourier transformation or Fast Fourier transformation on x(t) such that the frequency domain function 330 is obtained, where x'(w) in FIG. 3 represents the frequency domain function 330 of x(t). In one embodiment, the digital stethoscope 110 can then use x'(w) to perform its calculations and computations. Similarly, in one embodiment, the receiver module 304 can convert the acceleration data 272 from a time function 302 to a frequency domain function 330 using similar techniques.

In one embodiment, once the receiver module 304 receives the auditory signals 262, the accelerometer data 272, or a combination thereof and converts the signals from a time function 302 to frequency domain functions 330, the receiver module 304 can pass control and the frequency domain functions 330 to the subtraction module 306. The subtraction module 306 can enable the adjusting the auditory signals 262 received from the receiver module 304 by removing or filtering of unwanted auditory signals 262, for example a background noise created by the movement of the patient and picked up by the accelerometer 226, or other noise signals originating external to the patient's body, to obtain a noise free or nearly noise free auditory signals 262. The subtraction module 306 can enable the removal or filtering of unwanted auditory signals 262 by implementing a filter to remove unwanted sound frequencies. In one embodiment, the filter can be implemented using hardware, software, or a combination thereof. For example, the filter can be implemented to perform the functions of, or be, a low pass filter, a high pass filter, a bandpass filter, a Butterworth filter, a Chebyshev filter, a Bessel filter, a Elliptic filter, or a combination thereof.

In one embodiment, the subtraction module 306 can implement the filter such that the filter performs removal or filtering based on equation (2) below:

$$x(w)=y(w)-(\alpha\beta\Delta N(w)) \quad (2)$$

In equation (2), x(w) represents the filtered frequency domain function 330 of the auditory signals 262, accelerometer data 272, or a combination thereof obtained from the receiver module 304, y(w) represents the frequency domain function 330 of the auditory signals 262, accelerometer data 272, or a combination thereof obtained from the receiver module 304 that should be kept by the digital stethoscope 110, N(w) represents the frequency domain function 330 of the auditory signals 262, accelerometer data 272, or a combination thereof obtained from the receiver module 304 that should not be kept by the digital stethoscope 110, and $\alpha$, $\beta$, and $\Delta$ are variables that can be integers or whole numbers used to determine how much of N(w) should be subtracted from y(w) such that a low noise or noise free signal remains. In one embodiment, $\alpha$, $\beta$, and $\Delta$ can be varied or adjusted over time based on the noise conditions in which the digital stethoscope 110 is used. For example, in one embodiment, $\alpha$, $\beta$, and $\Delta$ can be varied or adjusted every 20, 50, or 100 milliseconds. In one embodiment, $\alpha$, $\beta$, and $\Delta$ can be varied or adjusted wherein $\alpha$, $\beta$, and $\Delta$ are large values in a high noise environment, such as a noisy office environment, or small values in a low noise environment, such as a quiet office environment. In one embodiment, $\alpha$, $\beta$, and $\Delta$ can be a set of pre-determined values. In another embodiment, $\alpha$, $\beta$, and $\Delta$ can change dynamically based on changes in the noise levels detected by the digital stethoscope 110. In one embodiment, $\alpha$, $\beta$, and $\Delta$ can be pre-configured values in the first FPGA 216 or can be obtained from the base station 118, the remote server 242, or a combination thereof.

In one embodiment, once the subtraction module 306 performs its adjustment and filtering of the auditory signals 262, the accelerometer data 272, or a combination thereof, the subtraction module 306 can pass control and the filtered frequency domain functions 330 of the auditory signals 262 to the filter module 308. The filter module 308 enables the generation of an auditory spectrogram 312 by further separating or filtering the filtered frequency domain functions 330 of the auditory signals 262, accelerometer data 272, or a combination thereof into one or more frequency bands 336 representing the different audible frequencies of the filtered frequency domain functions 330 of the auditory signals 262, the accelerometer data 272, or a combination thereof.

The auditory spectrogram 312 refers to a two dimensional visual representation of the spectrum of frequencies of the filtered frequency domain functions 330 of the auditory signals 262, the accelerometer data 272, or a combination thereof. The auditory spectrogram 312 can be represented as a chart, image, matrix, heat map, or other visual depiction showing a plot of the frequencies and the magnitudes associated with the frequencies of the filtered frequency domain functions 330 of the auditory signals 262, accelerometer data 272, or a combination thereof. The auditory spectrogram 312 can enable the sharpening or amplification of the frequency components filtered frequency domain functions 330 of the auditory signals 262, accelerometer data 272, or a combination thereof to better depict what sounds, noises, or acoustic tones are present in the filtered frequency domain functions 330 of the auditory signals 262, accelerometer data 272, or a combination thereof. The auditory spectrogram 312 can be used in the processing of the filtered frequency domain functions 312 of the auditory signals 262, accelerometer data 272, or a combination thereof to detect the respiratory abnormality, and result in more accurately determining the respiratory abnormality due to the ability of the auditory spectrogram 312 to sharpen and amplify the frequency components of the filtered frequency domain functions 330 of the auditory signals 262, accelerometer data 272, or a combination thereof.

In one embodiment, the filter module 308 can generate the auditory spectrogram 312 by implementing one or more cochlear filters 332 which the filtered frequency domain functions 330 of the auditory signals 262, accelerometer data 272, or a combination thereof can be passed through, and wherein the cochlear filters 332 are based on a cochlear model 314. The cochlear model 314 refers to the mathematical model or representation of the mechanics of a mammalian cochlea. In one embodiment, the cochlear model 314 can be implemented using hardware, software, or a combination thereof. For example, the cochlear filters 332 can include processors, active and passive components, circuitry, control logic, or a combination thereof implementing the cochlear model 314. In one embodiment, the cochlear filters 332 can separate different audible frequencies into one or more frequency ranges that a mammalian cochlea can hear.

For example, in one embodiment, the filter module 308 can implement one hundred and twenty-eight (128) cochlear filters 332 representing the one hundred and twenty eight different frequency ranges that can be heard by the mammalian cochlea. As such, the filter module 308 can mimic the human ear. In one embodiment, the output of the filter module 308 based on further filtering using the cochlear filters 332, the filtered frequency domain functions 330 of the auditory signals 262, accelerometer data 272, or a combination thereof is the auditory spectrogram 312. The auditory spectrogram 312 can visually represent the frequency ranges obtained from further filtering the filtered frequency domain functions 330 of the auditory signals 262, accelerometer data 272, or a combination thereof.

In one embodiment, once the filter module 308 generates the auditory spectrogram 312, the filter module 308 can pass control and the auditory spectrogram 312 to the convolution neural network module 310. The convolution neural network module 310 can enable the detection of the respiratory abnormality by performing a convolution procedure 316 on the auditory spectrogram 312 and further passing the results to a neural network 326 for classification as "normal" or "abnormal." The designation of "normal" or "abnormal" indicates whether the auditory signals 262, accelerometer data 272, or a combination thereof detected by the digital stethoscope 110 indicates a respiratory abnormality.

The convolution procedure 316 refers to a mathematical operation on two functions to produce a third function that expresses how the shape of one of the functions is modified by the other function. In one embodiment, the convolution procedure 316 can be implemented based on equation (3) below:

$$f[x, y] * g[x, y] = \sum_{n_1=-\infty}^{\infty} \sum_{n_2=-\infty}^{\infty} f[n_1, n_2] \cdot g[x - n_1, y - n_2] \quad (3)$$

$$f[x, y] * g[x, y] = \sum_{n_1=-\infty}^{\infty} \sum_{n_2=-\infty}^{\infty} f[x - n_1, y - n_2] \cdot g[n_1, n_2]$$

In equation (3), f*g represents the third function, "f" and "g" represent the two functions that the convolution procedure 316 is being performed on, x and y represent variables that the functions "f" and "g" depend on, and "n1" and "n2" represent an amount of shift. In one embodiment, the convolution neural network module 310 can implement the convolution procedure 316 using hardware, software, or a combination thereof. For example, the convolution neural network module 310 can include processors, active and passive components, circuitry, control logic, or a combination thereof implementing the convolution procedure 316.

In one embodiment, the auditory spectrogram 312 can represent one of the functions in equation (3), for example "f." In one embodiment, the convolution neural network module 310 can perform the convolution procedure 316 on the auditory spectrogram 312 by convoluting the auditory spectrogram 312 with a further function, for example one or more convolution functions 318, which can represent "g" in equation (3). In one embodiment, the convolution functions 318 can be one or more matrices of size N×N, where N represents an integer. For example, the convolution functions 318 can be a 3×3 matrix, 5×5 matrix, 10×10 matrix, or any other sized matrix. In one embodiment, the convolution functions 318 can further have one or more values represented by integers or whole numbers for their N×N elements. The one or more values can be the same or different for each N×N element. The one or more values can further be the same or different for each of the convolution functions 318.

In one embodiment, the one or more values of the convolution functions 318 can be obtained through a training process in which the one or more values are obtained through back propagation of machine learned trained data. The machine learned trained data can be, for example previous auditory spectrograms 312 representing known respiratory abnormalities, for example sounds, noises, auditory tones, or a combination thereof caused by a cough, a crackle, a wheeze, an asthma attack or other respiratory event or respiratory condition. The back propagation can generate the one or more values of the convolution functions 318 by calculating and attempting to reconstruct a known output, such as previously analyzed auditory spectrograms 312 representing known respiratory abnormalities, and determining what values the convolution functions 318 must have to reconstruct the previously analyzed auditory spectrograms 312 representing known respiratory abnormalities.

As such, the one or more values of the convolution functions 318 can be obtained and can be optimized to extract one or more features, such as curves, peaks, valleys, shapes, lines, or colors represented in the previously analyzed auditory spectrogram 312 which can be used to reconstruct the previously analyzed auditory spectrograms 312. Once determined, the one or more values of the convolution functions 318 can further be used to subsequently recognize the same features in further auditory spectrograms 312, such that the convolution functions 318 can be used to recognize respiratory abnormalities from auditory signals 262, accelerometer data 272, or a combination thereof detected by the digital stethoscope 110.

Continuing with the example, once the convolution functions 318 and their values are generated, the convolution neural network module 310 can perform the convolution procedure 316 on the auditory spectrogram 312 using the convolution functions 318 by performing the convolution procedure 316 over N×N frames of the auditory spectrogram 312 and multiplying the values of the N×N frame of the auditory spectrogram 312 with the values of the convolution functions 318. As a result, a further matrix is generated with one or more convolution values 320 representing the extracted features of the auditory spectrogram 312 for that N×N frame. The convolution values 320 can be integers or whole numbers that give quantified values to the features of the auditory spectrogram 312 for a particular N×N frame. By way of example, in areas where the auditory spectrogram 312 has a value greater than 0, the convolution values 320 generated can be positive integers assuming the one or more values of the convolution functions 318 are also non-zero. However, in areas where the auditory spectrogram 312 has a zero value, the convolution values 320 generated can be zero.

In one embodiment, the convolution procedure 316 can be performed repeatedly to successively compress the auditory spectrogram 312 into one or more convolution matrices 322, each having less rows and columns than the previous convolution matrices 322 generated as a result of the convolution procedure 316. In one embodiment, the generation of the subsequent convolution matrices 322 can depend on the values of the previous convolution matrices 322. For example, in one embodiment, if two convolution matrices 322 are generated as a result of the convolution procedure 316, the first can have the size M×M and the second can have the size T×T, wherein the second can have its convolution values 320 depend on the first, and where M>T. In one embodiment, the convolution matrices 322 can be stored in the first DRAM, wherein the convolution matrices 322 can be used in successive calculation of further convolution matrices 322.

In one embodiment, as a result of performing the convolution procedure 316 successively, a convolution vector 324 can be generated containing convolution values 320. For example, in one embodiment, the convolution vector 324 can be an M×1 vector, where M is an integer, such as a 20×1 vector, containing convolution values 320. In one embodiment, the convolution vector 324 can be used as the input to a machine learning process, for example the neural network 326, which can be used to determine whether the convolution vector 324 representing a compressed version of the auditory spectrogram 312, accelerometer data 272, or a combination thereof indicates a respiratory abnormality. The neural network 326 refers to an interconnected group of artificial neurons that uses a mathematical or computational model for information processing based on a connectionistic approach to computation.

The neural network 326 can use the weights 276 of FIG. 2C and one or more biases 334 for each of its nodes or neurons which can be used to determine whether the auditory signals 262 represent a respiratory abnormality. Biases 334 refer to values, variables, parameters, or a combination thereof which enables the neural network 326 to better fit the data to assist the neural network 326 to learn patterns. In one embodiment, the weights 276 and biases 334 can be integers or whole numbers. The weights 276 and biases 334 can connect nodes or neurons of the neural network 326, and can determine the strength of each connection between each node or neuron such that the higher the value for the weights 276 and biases 334 for a given connection, the more the connection will affect the overall computations and outcomes of the neural network 326. In one embodiment, the weights 276 and biases 334 can be determined and obtained in a similar process of back propagation of training data similar to what was described above with respect to the one or more values of the convolution functions 318. For the purposes of discussion, it is assumed that the weights 276 and biases 334 are already known and optimized for detecting the respiratory abnormality.

Continuing with the example, in one embodiment, the neural network 326 can further have a confidence level 328 associated with its output. The confidence level 328 can be a value, variable, parameter, or a combination thereof which, if the output of the neural network 326 exceeds, the neural network 326 can determine that the output can be classified as either "normal" or "abnormal." By way of example, if the confidence level 328 is set to for example "90%," any output of the neural network 326 indicating that the neural network 326 believes the auditory signals 262, accelerometer data 272, or a combination thereof detected is greater than or equal to 90% "normal" or "abnormal" will be accepted as a valid result and classified accordingly by the neural network 326. In one embodiment, if the confidence level 328 is met or exceeded as a result of the processing by the neural network 326, the digital stethoscope 110 can generate the classification value 266 indicating a "normal" or "abnormal" classification, and display an indicator based on the classification value 266, such as a red or green colored light, or a message indicating that the auditory signals 262 are "abnormal" or "normal."

It has been discovered that the use of the convolutional neural network module 310 described above allows the digital stethoscope 110 to generate the classification value 266 and display the indicator in real time when used in conjunction with the architecture of the digital stethoscope 110 because it uses less computing resources, such as processing power and memory as opposed to conventional methods of detecting a respiratory abnormality. Real time refers to the instance where the classification value 266 and the indicator can be displayed almost instantly or within milliseconds of receipt of the auditory signals 262, the accelerometer data 272, or a combination thereof by the digital stethoscope 110.

It has been further discovered that the ability to generate the classification value 266 and display the indicator in real time significantly improves the current state of the art by allowing patients or users of the system 100 to be notified of a respiratory abnormality instantaneously and seek treatment immediately. It has been further discovered that the ability of patients or users of the system 100 to be notified of the respiratory abnormality in real time can result in the ability to potentially save more patient lives by allowing patients to know that they need to seek medical treatment rapidly if a respiratory abnormality is detected.

Figure 4A:
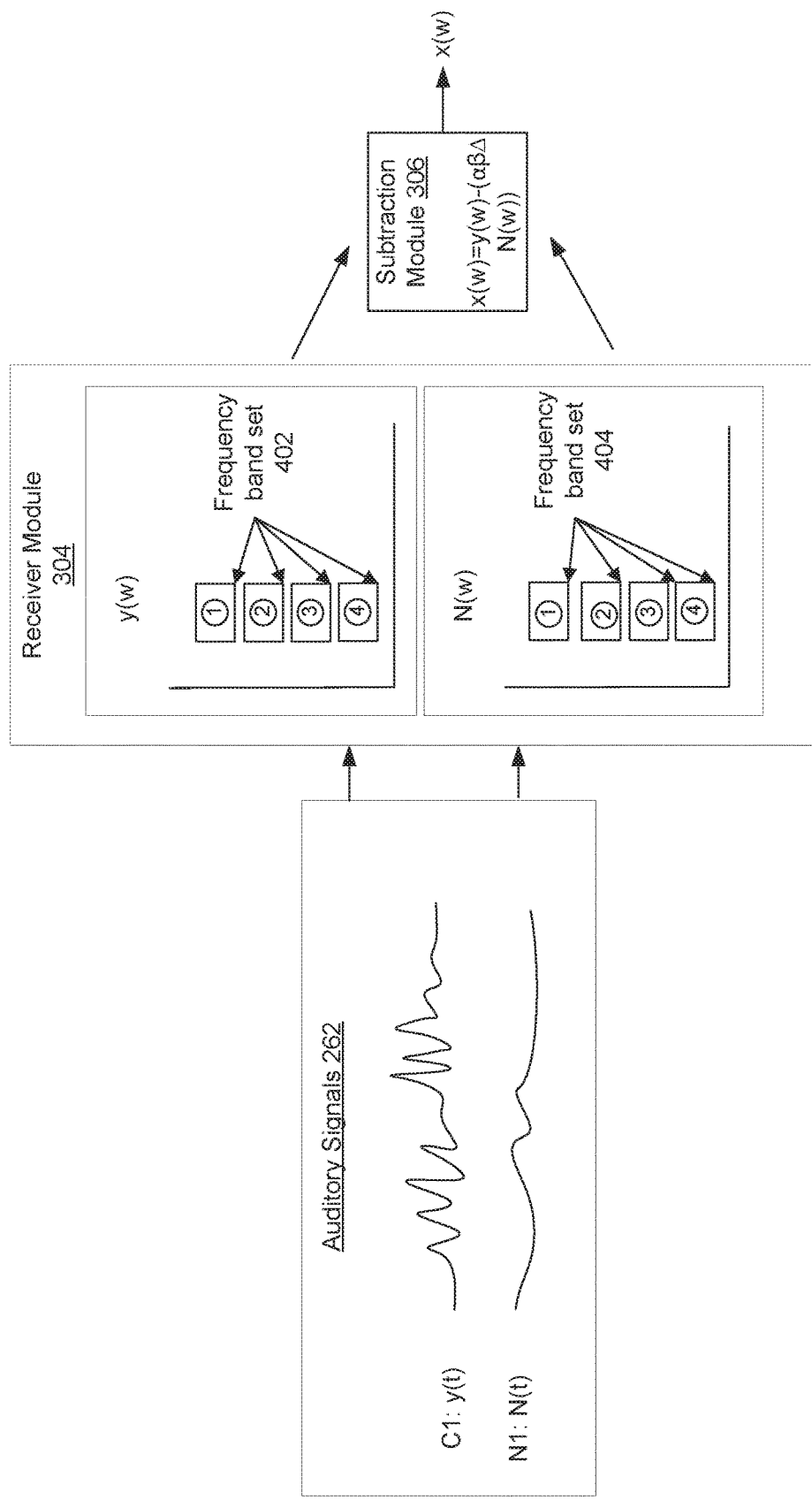
FIG. 4A is an exemplary depiction of the functioning of a receiver module and a subtraction module in an embodiment of the present invention.

Referring now to FIG. 4A, therein is shown an exemplary depiction of the functioning of the receiver module 304 and the subtraction module 306 in an embodiment of the present invention. In the embodiment shown in FIG. 4A, once the auditory signals 262 are received, by the receiver module 304, the auditory signals 262 can be converted from time functions 302 to frequency domain functions 330 as discussed previously with respect to FIG. 3. By way of example, FIG. 4A shows two frequency domain functions y(w) and N(w). In the embodiment shown in FIG. 4, y(w) can represent the frequency domain function 330 of auditory signals 262 obtained by the receiver module 304 that should be kept by the digital stethoscope 110 while N(w) can represent the frequency domain function 330 of auditory signals 262 obtained by the receiver module 304 that should not be kept by the digital stethoscope 110. Further, y(w) and N(w) are shown as containing one or more frequencies as depicted by a first frequency band set 402 and a second frequency band set 404. The first frequency band set 402 and the second frequency band set 404 represent the different frequencies contained within y(w) and N(w) and can be obtained by converting the time functions 302 to the frequency domain functions 330. For example, in one embodiment, boxes labeled as "1" of the first frequency band set 402 or the second frequency band set 404 can represent an audible portion of y(w) or N(w) that has a high frequency, while boxes labeled as "4" of the first frequency band set 402 or the second frequency band set 404 can represent an audible portion of y(w) or N(w) that has a low frequency. In one embodiment, y(w) and N(w) can be passed to the subtraction module 306 so that the subtraction module 306 can filter out any unwanted noise portions, for example all or some of N(w) according to equation (2) above for each of the first frequency band set 402 and the second frequency band set 404.

Figure 4B:
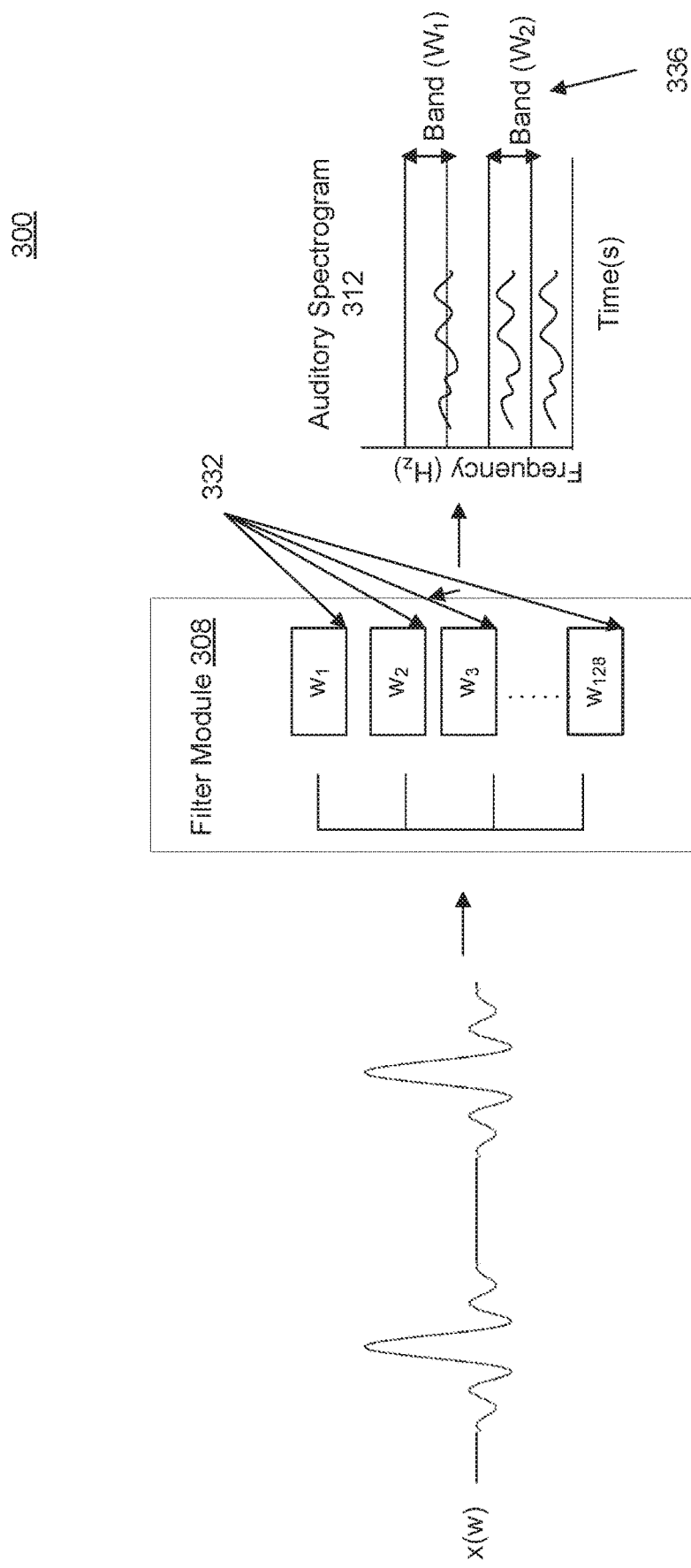
FIG. 4B is an exemplary depiction of the functioning of a filter module and the generation of an auditory spectrogram in an embodiment of the present invention.

Referring now to FIG. 4B, therein is shown an exemplary depiction of the functioning of the filter module 308 and the generation of the auditory spectrogram 312 in an embodiment of the present invention. In the embodiment shown in FIG. 4B, the filtered frequency domain functions 330 of the auditory signals 262 is shown as being passed to the filter module 308. The filter module 308 is further shown with the cochlear filters 332. In one embodiment, the filtered frequency domain functions 330 of the auditory signals 262 can pass through the cochlear filters 332. As a result of passing the filtered frequency domain functions 330 of the auditory signals 262 through the cochlear filters 332, the auditory spectrogram 312 is generated. The auditory spectrogram 312 can be generated by, for example plotting the frequencies filtered by the cochlear filters 332 on a plot showing time versus frequency. In one embodiment, the auditory spectrogram 312 can further indicate the frequency bands 336 of the auditory signals 262.

Figure 4C:
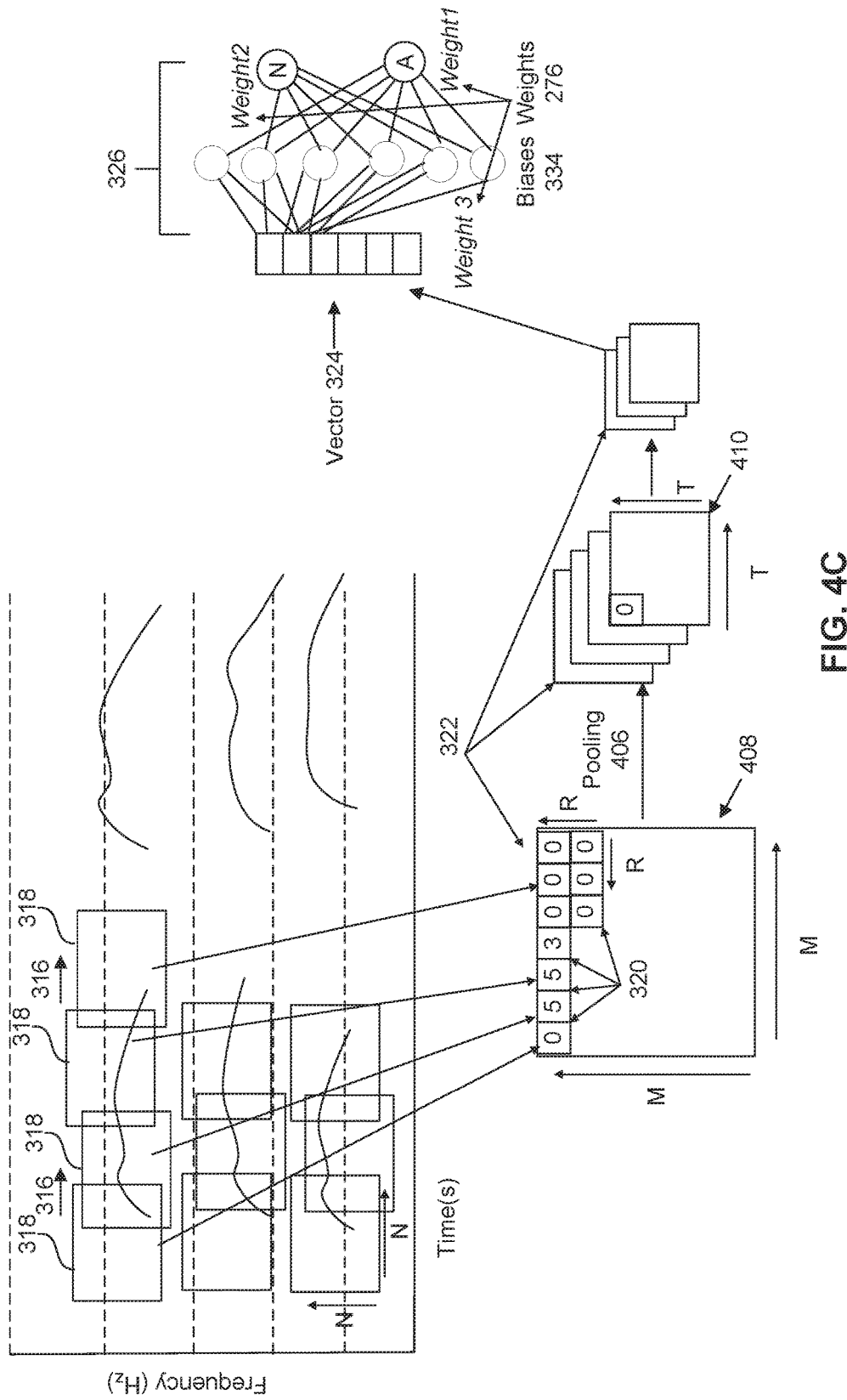
FIG. 4C is an exemplary depiction of the functioning of a convolution neural network module in an embodiment of the present invention.

Referring now to FIG. 4C, therein is shown an exemplary depiction of the functioning of the convolution neural network module 310 in an embodiment of the present invention. In the embodiment shown in FIG. 4C, the auditory spectrogram 312 is shown. Further, the convolution functions 318 are shown as being represented by the one or more boxes representing matrices of size N×N. The convolution neural network module 310 can perform the convolution procedure 316 by convoluting the auditory spectrogram 312 with the convolution functions 318 by shifting the convolution functions 318 over the auditory spectrogram 312 and multiplying the values for N×N frames of the auditory spectrogram 312 with the values of the convolution functions 318. As a result, the convolution matrices 322 are generated with convolution values 320. FIG. 4C further depicts the generation of the subsequent convolution matrices 322. In one embodiment, the subsequent convolution matrices 322 can be generated by for example a pooling process 406, in which subsequent convolution matrices 322 are generated by reducing the dimensions of the previous convolution matrices 322 generated.

By way of example, a first convolution matrix 408 can be generated as a result of the convolution procedure 316. In one embodiment, a second convolution matrix 410 can subsequently be generated based on the first convolution matrix 408 by the pooling process 406, by for example, taking groups of sub-elements of the first convolution matrix 408 and generating the second convolution matrix 410 based on the sub-elements. For example, if the first convolution matrix 408 is an M×M sized matrix, the first convolution matrix 408 can be broken down into sub-matrices, for example R×R sized sub-matrices, and a value chosen from the R×R sub-matrix can be taken as one of the convolution values 320 of the second convolution matrix 410. The pooling process 406 can be done in a variety of ways, including max pooling in which the maximum value for the R×R sub-matrix is taken as one of the convolution values 320 of the second convolution matrix 410. In another embodiment, the pooling process 406 can be done by average pooling in which the values of the R×R sub-matrix are averaged and the average is taken as one of the convolution values 320 of the second convolution matrix 410.

In one embodiment, the pooling process 406 can be done repeatedly to successively compress the auditory spectrogram 312 and generate the convolution vector 324. The convolution vector 324 can then be input to the neural network 326 which can use the weights 276 and biases 334 to determine whether the convolution vector 324 represents a respiratory abnormality by classifying the convolution values 320 associated with the convolution vector 324 as being "normal" or "abnormal."

In one embodiment, the second control flow 300 described above can further be used to make other classifications based on the auditory signals 262 detected by the digital stethoscope 110. For example, in addition to detecting a respiratory abnormality and making a classification of "normal" or "abnormal," the digital stethoscope 110 can classify the auditory signals 262 as a particular type of sound, noise, acoustic tone, or a combination thereof using the same processes described above with respect to the control flow 300. For example, in one embodiment, the digital stethoscope 110 using the second control flow 300, can classify the auditory signals 262 as a wheeze, a crackle, or a cough based on the convolutional neural network module 310 having its convolution functions 318 and neural network 326 trained to recognize a wheeze, a crackle, or a cough based on training with machine learned trained data representing known sounds, noises, auditory tones, or a combination thereof caused by a cough, a crackle, a wheeze, or a combination thereof. As such, the classifications such as "cough" or "no cough," "crackle" or "no crackle," or "wheeze" or "no wheeze" can be generated.

In one embodiment, the coughs, crackles, or wheezes detected can be saved in the configuration file 264 as the cough count 274 and can be used to predict a future respiratory event or respiratory condition. For example, if the cough count 274 is known and exceeds a certain threshold, for example, is greater than the average number of coughs for the patient within a certain time period, and the digital stethoscope 110 further detects that the coughs indicate a respiratory abnormality, the digital stethoscope 110 can, for example, further generate a parameter, value, or variable indicating that a respiratory event or respiratory condition is likely in the future and save the information in the configuration file 264, which can further be shared with the base station 118, the remote server 242, or a combination thereof to alert the patient or a user of the system 100 of the likelihood of the respiratory event or respiratory condition. In one embodiment, the prediction of the respiratory event or respiratory condition can further be aided by the use of machine learning processes, for example a long short term memory (LSTM) network model. The LSTM network model will be discussed further below.

Forecasting Using an LSTM

Figure 5A:
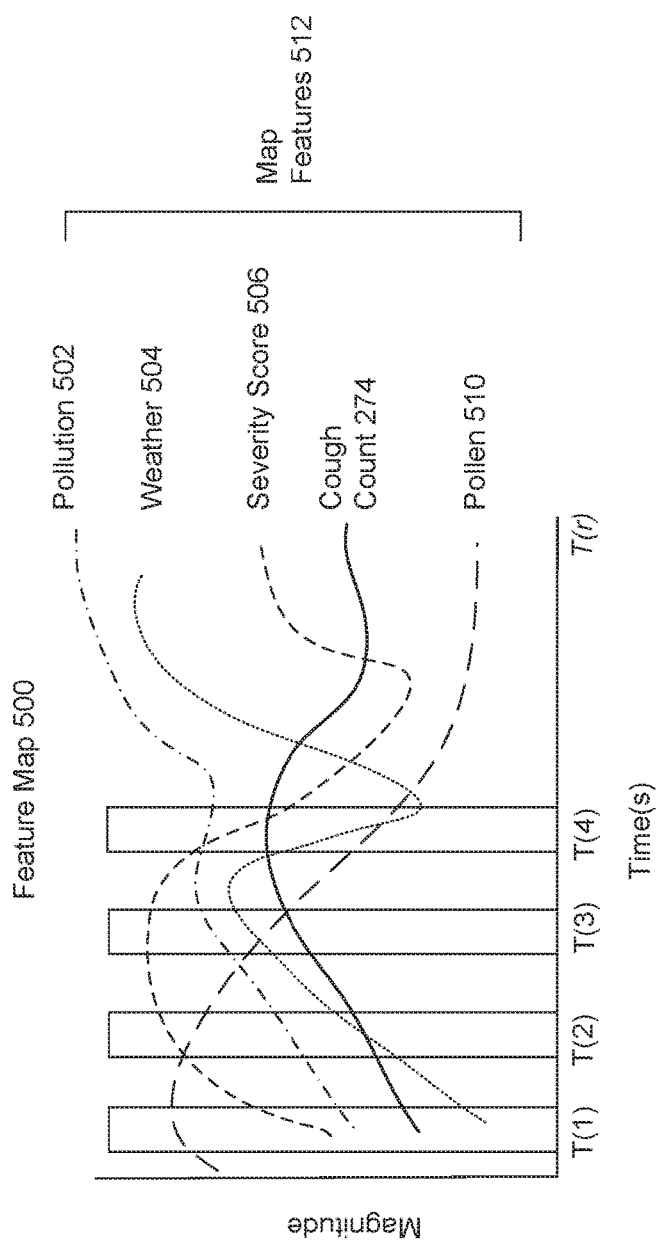
FIG. 5A is an exemplary feature map used to predict a respiratory event or respiratory condition in the future in an embodiment of the present invention.

Referring now to FIG. 5A, therein is shown an exemplary feature map 500 used to predict a respiratory event or respiratory condition in the future in an embodiment of the present invention. The feature map 500 is a chart, image, matrix, plot, or other visual depiction showing one or more map features 512 versus time. In one embodiment, the feature map 500 can be generated by the digital stethoscope 110, the base station 118, the remote server 242, or a combination thereof. The map features 512 refer to parameters, variables, or a combination thereof that are used to predict a respiratory event or respiratory condition in the future. The map features 512 describe one or more conditions at a particular time or over a period of time that can affect the onset of a respiratory event or respiratory condition.

For example, in one embodiment, the map features 512 can include, environmental data, data regarding the patient, or a combination thereof, indicating an environmental condition at a particular time or over a period of time affecting the onset of a respiratory event or respiratory condition, or patient data, including data regarding coughs, crackles, wheezes, or a combination thereof, indicating the onset of a respiratory event or respiratory condition. For example, the map features 512 can include environmental data indicating how much pollution is in the air at a particular time, how much pollen is in the air at a particular time, the air quality at a particular time, or can include data regarding the patient, such as data regarding whether the patient is coughing or wheezing at a certain time, the severity of the patient's cough, crackle, or wheeze at a certain time, how many times a patient is coughing or wheezing over a period of time, or a combination thereof. As such, the map features 512 can include a pollution level data 502, a weather data 504, a severity score 506 indicating how severe a patient's cough, crackle, wheeze, respiratory event, or respiratory condition is at a given time, the cough count 274, a pollen data 510, or a combination thereof.

In one embodiment the severity score 506 can be categorized indicating the level of severity of the patient's cough, crackle, wheeze, respiratory event, or respiratory condition at a given time. In one embodiment, the categorization can be, for example on a scale of 1-6 where, 1 indicates no or non-present severity, 2 indicates intermittent severity, 3 indicates mild severity, 4 indicates moderate severity, 5 indicates severe or high severity, and 6 indicates acute severity in which the patient should get immediate medical attention. In one embodiment, the severity score 506 can be determined by the digital stethoscope 110, the base station 118, the remote server 242, or a combination thereof by analyzing the auditory signals 262 received from the digital stethoscope 110, and analyzing the auditory signals 262 pursuant to the second control flow 300 or equivalent control flow to determine the category of the severity score 506, wherein the neural network 326 or a further neural network can be used to determine the category of the severity score 506.

Continuing with the example, in one embodiment, the map features 512 can be obtained from the digital stethoscope 110, the base station 118, or a combination thereof, and the components thereof including for example the microphones 106, the air quality sensors 116, or a combination thereof. In one embodiment, the map features 512, the feature map 500, or a combination thereof can be used as an input to a machine learning process that can be used to predict a respiratory event or respiratory condition in the future. For example, the map features 512, the feature map 500, or a combination thereof can be the input to an LSTM process 514 to predict the respiratory event or respiratory condition in the future. In one embodiment, more than one feature map 500 can be the input to the LSTM process 514 to predict the respiratory event or respiratory condition in the future. The LSTM process 514 refers to artificial recurrent neural network (RNN) architecture which uses feedback to make predictions about future events.

Figure 5B:
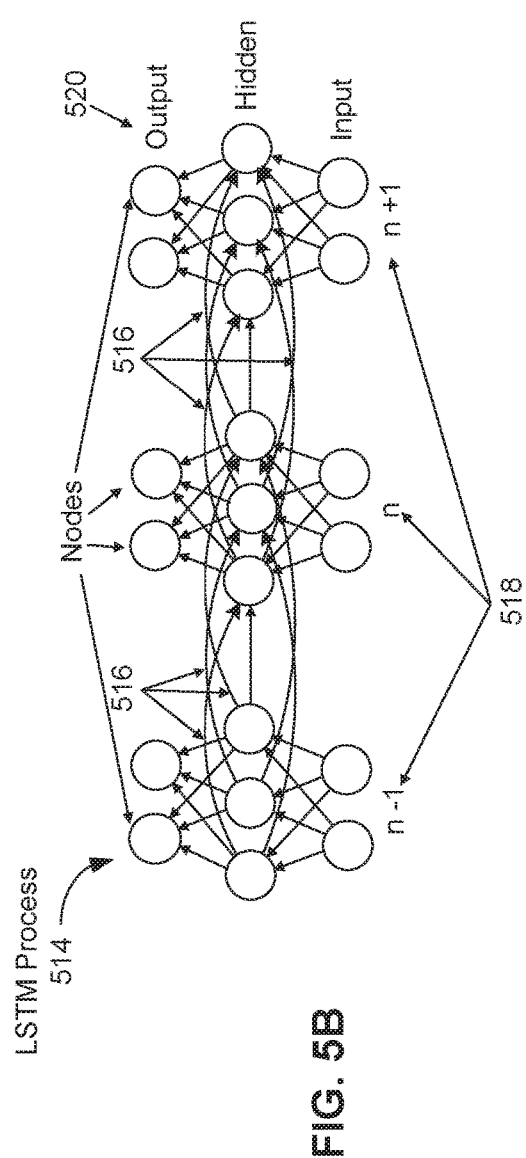
FIG. 5B is an exemplary depiction of an LSTM process used to predict a third respiratory event occurring for the patient at a future time in an embodiment of the present invention.

Referring now to FIG. 5B, therein is shown an exemplary depiction of the LSTM process 514 used to predict a third respiratory event 520 occurring for the patient at a future time in an embodiment of the present invention. The LSTM process 514 of FIG. 5B can work in the following manner. In the embodiment of FIG. 5B, one or more time buckets 518 are shown as represented by "n−1," "n," and "n+1," wherein the time buckets 518 contain information regarding the map features 512 at a particular instance of time or over a period of time. In one embodiment, the time buckets 518 can be implemented as data structures, variables, parameters, or a combination thereof as nodes in the LSTM process 514. In one embodiment, each instance of the time buckets 518 can be predicted by implementing a look back feature 516, which references the map features 512 of previous time buckets 518 and performs a probability calculation to determine the likelihood that future time buckets 518 will have map features 512 exhibiting certain characteristics or having certain values. For example, "n" can be predicted by referencing the map features 512 of "n−1," and "n+1" can further be predicted by referencing the map features 512 of "n−1," "n," and so forth.

In one embodiment, the prediction is done by comparing the map features 512 of past time buckets 518 to one another and finding one or more patterns or correlations between the map features 512. The patterns or correlations can be, for example, map features 512 indicating a high probability of exhibiting a certain characteristic or having a certain value based on one or more previous map features 512 exhibiting certain characteristics or having certain values. By way of example, if it is determined that when pollution is high and a patient has a certain number of coughs during the period when the pollution is high, there is a high probability that the severity scores 506 of a patient's coughs, crackles, or wheezes will be "5"-severe or "6"-acute, the LSTM process 514 can look for that pattern or correlation when comparing the map features 512 of past time buckets 518, and if that pattern or correlation is detected, can predict that in instances where a pollution level is getting to a high level and the patient has a certain number of coughs building up to a certain threshold, the severity score 506 of those coughs is likely to be "5"-severe or "6"-acute in the near future. The example is merely exemplary and not meant to be limiting.

In one embodiment, the LSTM process 514 can contain weights 276 associated with the look back feature 516, similar to the weights 276 described with respect to FIG. 2C.

The weights 276 can be used to determine the strength of each connection between the time buckets 518 such that the higher the value for the weights 276 for a given look back feature 516, the more the map features 512 of the particular time buckets 518 associated with the look back feature 516 will affect the overall computations and predictions of the LSTM process 514. In one embodiment, the weights 276 can be determined and obtained in a similar process of back propagation of training data similar to what was described above with respect to the one or more values of the convolution functions 318. For the purposes of discussion, it is assumed that the weights 276 are already known and optimized for predicting map features 512 for future time buckets 518 based on a history of known map features 512 associated with known respiratory events and respiratory conditions.

In one embodiment, the predictions made by the LSTM process 514 can further be output to the digital stethoscope 110, the base station 118, the remote server 242, or a combination thereof. For example, if the LSTM process 514 predicts that a patient will have a severe or acute respiratory event or respiratory condition in the near future, an output can be generated indicating the likelihood of the respiratory event or respiratory condition to, for example, the display unit 102 of the digital stethoscope 110 indicating the prediction.

It has been discovered that the use of the LSTM process 514 described above allows the digital stethoscope 110, the base station 118, or the remote server 242 to generate accurate predictions for the likelihood of occurrence of respiratory events or respiratory conditions. It has been further discovered that the ability to generate predictions regarding respiratory events or respiratory conditions significantly improves the current state of the art by allowing patients or users of the system 100 to be notified of respiratory events or respiratory conditions before they occur and allow patients or users of the system 100 to seek treatment in advance of a medical emergency. It has been further discovered that the ability of patients or users of the system 100 to be notified of the respiratory events or respiratory conditions can result in the ability to potentially save more patient lives by allowing patients to know that they need to seek medical treatment rapidly if a respiratory event or respiratory condition is predicted.

Convolutional Auto-Encoder to Predict Future Respiratory Noises

Figure 6:
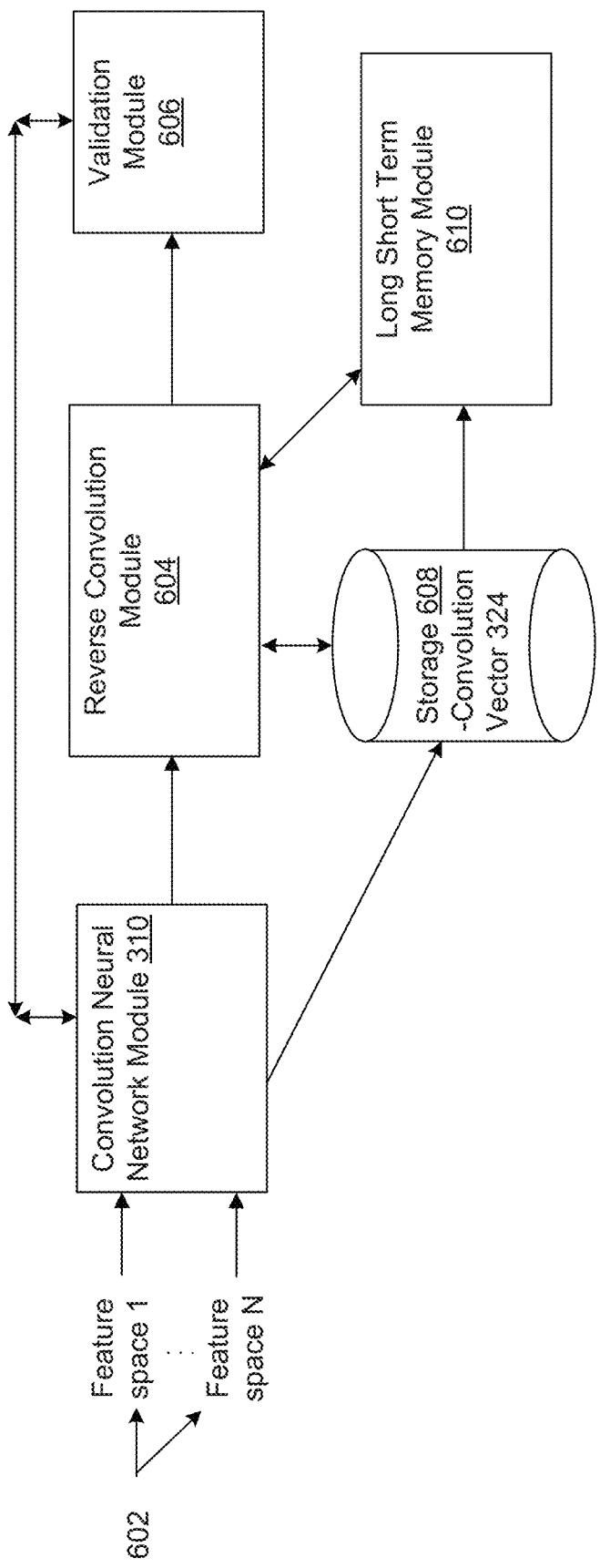
FIG. 6 is an exemplary third control flow for forecasting characteristics of a future respiratory event or respiratory condition in an embodiment of the present invention.

Referring now to FIG. 6, therein is shown an exemplary third control flow 600 for forecasting characteristics of a future respiratory event or respiratory condition in an embodiment of the present invention. For brevity of description, in this embodiment, the third control flow 600 will be described as being performed using the base station 118. This description is merely exemplary and not meant to be limiting. In other embodiments, the third control flow 600 can be performed using the digital stethoscope 110, the remote server 242, or a combination thereof.

The third control flow 600, can enable forecasting characteristics of a future respiratory event or respiratory condition by using one or more feature spaces 602 generated based on the auditory signals 262, wherein the feature spaces 602 are a three dimensional map or representation of the auditory signals 262. In one embodiment, the feature spaces 602 can be generated by the base station 118, for example, by the second FPGA 244 after receiving the auditory signals 262. The feature spaces 602 can be a chart, image, matrix, plot, or other visual depiction representing the auditory signals 262 as a three dimensional map. The feature spaces 602 can have one or more variables with values representing characteristics of the auditory signals 262. For example, in one embodiment, the variables can include a frequency associated with the auditory signals 262 at a particular time, a rate representing a map of auditory nerve firing rate indicated by the auditory signals 262 at a particular time, and a severity representing the magnitude of the auditory signal 262 at a particular time. The feature spaces 602 can be generated using the same techniques as generating the auditory spectrogram 312, where the auditory signals 262 can be received, converted into the frequency domain functions 330, and filtered using the cochlear model 314 to obtain the variables of the feature spaces 602. Once the feature spaces 602 are generated, the third control flow 600 can be used to forecast characteristics of a future respiratory event or respiratory condition using the feature spaces 602.

The third control flow 600 can be implemented with modules and sub-modules, the components of the base station 118, or a combination thereof. In one embodiment, the third control flow 600 can include the convolution neural network module 310, a reverse convolution module 604, a validation module 606, and a long short term memory module 610. In one embodiment, the convolution neural network module 310 can couple to the reverse convolution module 604. The convolution neural network module 310 can further couple to the long short term memory module 610 via a storage 608. The reverse convolution module 604 can couple to the validation module 606.

In one embodiment, the convolution neural network module 310, as previously described with respect to FIG. 3, can receive the feature spaces 602 and perform the convolution procedure 316 on the feature spaces 602 to generate a convolution vector 324 for each of the feature spaces 602. In one embodiment, once the convolution vector 324 is generated, the convolution vector 324 can be saved in a storage 608 for later use by the long short term memory module 610. The storage 608 can be the second storage unit 248 or a further storage unit external to the base station 118, such as an external database, hard drive, volatile memory, nonvolatile memory, or a combination thereof.

In one embodiment, once the convolution neural network 310 has completed the convolution procedure 316 for each of the feature spaces 602, each convolution vector 324 and control can further be passed to the reverse convolution module 604. The reverse convolution module 604 enables the reverse process of the convolution neural network module 310, such that the reverse convolution module 604 can decode and reconstruct the feature spaces 602 by, for example, reversing the computations done by the convolution neural network module 310 to generate the feature spaces 602 from the convolution vector 320. In one embodiment, the reversing of the convolution vector 324 can be used to forecast characteristics of a future respiratory event or respiratory condition as will be described below. The reverse convolution module 604 can perform the reverse process of the convolution neural network module 310, by for example performing a reverse of the convolution procedure 316 by undoing all the calculations performed by the convolution procedure 316.

In one embodiment, once the reverse convolution module 604 reconstructs the feature spaces 602, it can pass the reconstructed feature spaces 602 and control to the validation module 606. The validation module 606 enables the validation of the of the computations of the reverse convolution module 604 by for example comparing the reconstructed feature spaces 602 with the feature spaces 602 received by the convolution neural network module 310. For example, in one embodiment, the comparison can include comparing the values of the variables, for example the frequency, rate, and scale of each the reconstructed feature spaces 602 with the same variables for feature spaces 602 received by the convolution neural network module 310 and determining whether they are equal or within an error tolerance, such that the two can be considered equivalent. If the validation module 606 determines that the values are equivalent, the computations of the reverse convolution module 310 can be considered valid such that reverse convolution module 604 can later be used to forecast characteristics of a future respiratory event or respiratory condition.

In one embodiment, once the validation module 606 has validated the computations of the reverse convolution module 604, control can pass to the long short term memory module 610. The long short term memory module 610 can enable and implement the LSTM process 514 as described with respect to FIG. 5B. In one embodiment, the long short term memory module 610 can retrieve each saved convolution vector 324 from the storage 608 and perform the LSTM process 514 using each convolution vector 324 in a similar fashion as was described with the time buckets 518 of FIG. 5B. By way of example, the long short term memory module 610 can replace the time buckets 518 with each convolution vector 324 and predict a future convolution vector 324 using the values of each convolution vector 324.

In one embodiment, the long short term memory module 610 can look for patterns as described with respect to FIG. 5B using a look back feature 516 and weights 276 trained based on a history of respiratory events or respiratory conditions, but with respect to the convolution vectors 324 such that the long short term memory module 610 can forecast characteristics of a future respiratory event or respiratory condition based on each previous convolution vector 324.

By way of example, if the long short term memory module 610 determines that each previous convolution vector 324 indicates a trend towards feature spaces 602 for a known respiratory event or respiratory condition, the long short term memory module 610 can forecast characteristics of future feature spaces 602 such that the long short term memory module 610 can predict or forecast particular feature spaces 602 indicating a particular respiratory event or respiratory condition. In one embodiment, the forecasting can be done by generating a predicted convolution vector 324 with predicted values indicating the predicted or forecasted characteristics of the forecast feature spaces 602. The predicted or forecast feature spaces 602 can further be generated by decoding or reversing the predicted convolution vector 324 via the reverse convolution procedure module 604.

In one embodiment, the predicted or forecast feature spaces 602 can further be output to the digital stethoscope 110, the base station 118, the remote server 242, or a combination thereof. For example, if the long short term memory module 610 forecasts that a patient will have feature spaces 602 indicating a particular respiratory event or respiratory condition in the near future, an output can be generated indicating the forecast or predicted feature spaces 602 to, for example, the display unit 102 of the digital stethoscope 110 and an alert can be sent to the patient or user of the system 100 indicating the forecasting.

It has been discovered that the use of the third control flow 600 described above allows the digital stethoscope 110, the base station 118, or the remote server 242 to generate accurate predictions for the likelihood of occurrence of respiratory events or respiratory conditions without the need to know about environmental conditions at a particular time or over a period of time affecting the onset of a respiratory event or respiratory condition and can generate forecasts of characteristics of respiratory events or respiratory conditions based on the auditory signals 262. It has been further discovered that the ability to generate predictions regarding respiratory events or respiratory conditions significantly improves the current state of the art by allowing patients or users of the system 100 to be notified of a respiratory event or respiratory conditions before they occur and allow patients or users of the system 100 to seek treatment in advance of a medical emergency. It has been further discovered that the ability of patients or users of the system 100 to be notified of the respiratory events or respiratory conditions can result in the ability to potentially save more patient lives by allowing patients to know that they need to seek medical treatment rapidly if a respiratory event or respiratory condition is predicted.

Figure 7:
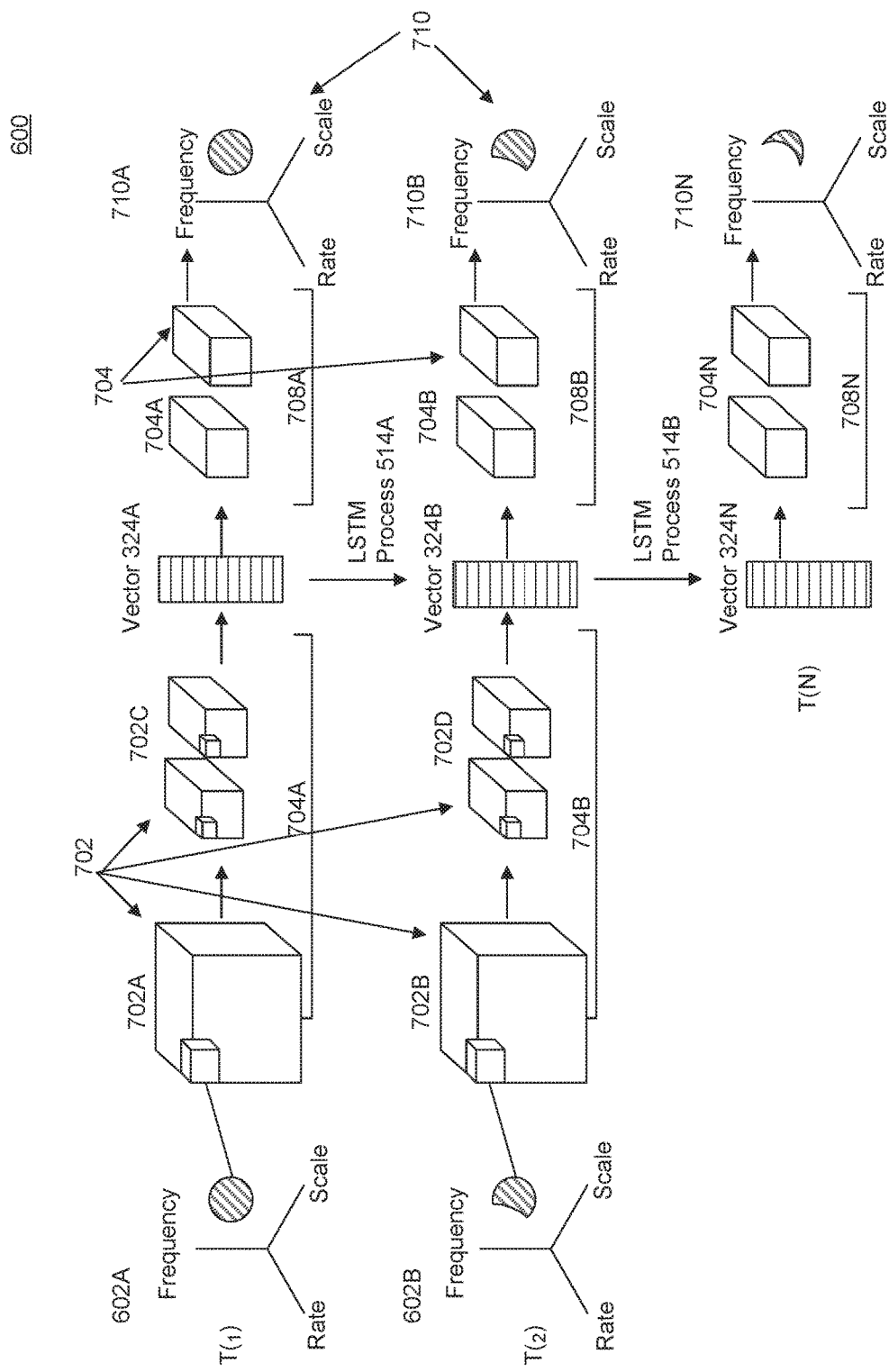
FIG. 7 is an exemplary depiction of the third control flow for forecasting characteristics of a future respiratory event or respiratory condition in an embodiment of the present invention.

Referring now to FIG. 7, therein is shown an exemplary depiction of the third control flow 600 for forecasting characteristics of a future respiratory event or respiratory condition in an embodiment of the present invention. In the embodiment of FIG. 7, two feature spaces 602 are shown, as indicated by 602A and 602B representing a frequency, rate, and scale of the auditory signals 262 at different times T(1) and T(2). FIG. 7 further shows 602A and 602B undergoing the convolution procedure 316, as indicated by 704A and 704B. As a result, one or more convolution matrix spaces 702 are generated, as indicated by 702A, 702B, 702C, and 702D. 702A, 702B, 702C, and 702D, similar to the convolution matrices 322, represent spaces generated from doing the convolution procedure 316 on three dimensional feature spaces 602, such that they represent three dimensional matrix spaces. FIG. 7 further shows the convolution matrix spaces 702 being compressed from one iteration of the convolution procedure 316 to the next such that the convolution matrix spaces 702 of a subsequent iteration are smaller than the convolution matrix spaces 702 of the previous iteration, similar to what was described with respect to FIGS. 3 and 4C, until the convolution matrix spaces 702 can be formed into a convolution vector 324 associated with each of the feature spaces 602. The convolution vector 324 associated with each of the feature spaces 602 are represented as 324A and 324B. FIG. 7, further shows the reversing or decoding of the convolution procedure 316, as indicated by 708A and 708B to generate one or more reverse convolution matrix spaces 704, as indicated by 704A and 704B. The reverse convolution matrix spaces 704 represent three dimensional matrix spaces generated from performing the reverse convolution procedure 316 on 324A and 324B. FIG. 7 further shows one or more reconstructed feature spaces 710, as indicated by 710A and 710B, generated based on performing the reversing of the convolution procedure 316 on the reverse convolution matrix spaces 704.

In the embodiment shown in FIG. 7, each of 324A and 324B can further be used to forecast characteristics of a future respiratory event or respiratory condition based on having the LSTM process 514, as done by the long short term memory module 610, performed using 324A and 324B as the inputs of the LSTM process 514. For example, FIG. 7 shows the LSTM process 514 performed, as indicated by 514A and 514B, such that a prediction vector 324N, representing a predicted convolution vector 324 is generated for a future time, indicated by T(N). The prediction vector 324N can have a reverse convolution procedure 316 performed on it, as indicated by 708N to generate a predicted feature space 710N representing the forecasted characteristics of a future respiratory event or respiratory condition.

The system 100 has been described with module functions or order as an example. The system 100 can partition the modules differently or order the modules differently. For example, the first software 224, the second software 252, or a combination thereof, can include the modules for the system 100. As a specific example, the first software 224, the second software 252, or a combination thereof can include the receiver module 304, the subtraction module 306, the filter module 308, the convolution neural network module 310, the reverse convolution module 604, the validation module 606, the long short term memory module 610, and associated sub-modules included therein.

The first control unit 210, the second control unit 236, or a combination thereof, can execute the first software 224, the second software 252, or a combination thereof, to operate the modules. For example, the first control unit 210, the second control unit 236, or a combination thereof, can execute the first software 224, the second software 252, or a combination thereof, to implement the receiver module 304, the subtraction module 306, the filter module 308, the convolution neural network module 310, the reverse convolution module 604, the validation module 606, the long short term memory module 610, and associated sub-modules included therein.

The modules described in this application can be implemented as instructions stored on a non-transitory computer readable medium to be executed by the first control unit 210, the second control unit 236, or a combination thereof. The non-transitory computer readable medium can include the first storage unit 218, the second storage unit 248, or a combination thereof. The non-transitory computer readable medium can include non-volatile memory, such as a hard disk drive, non-volatile random access memory (NVRAM), solid-state storage device (SSD), compact disk (CD), digital video disk (DVD), or universal serial bus (USB) flash memory devices. The non-transitory computer readable medium can be integrated as a part of the system 100 or installed as a removable portion of the system 100.

Exemplary Methods

Figure 8:
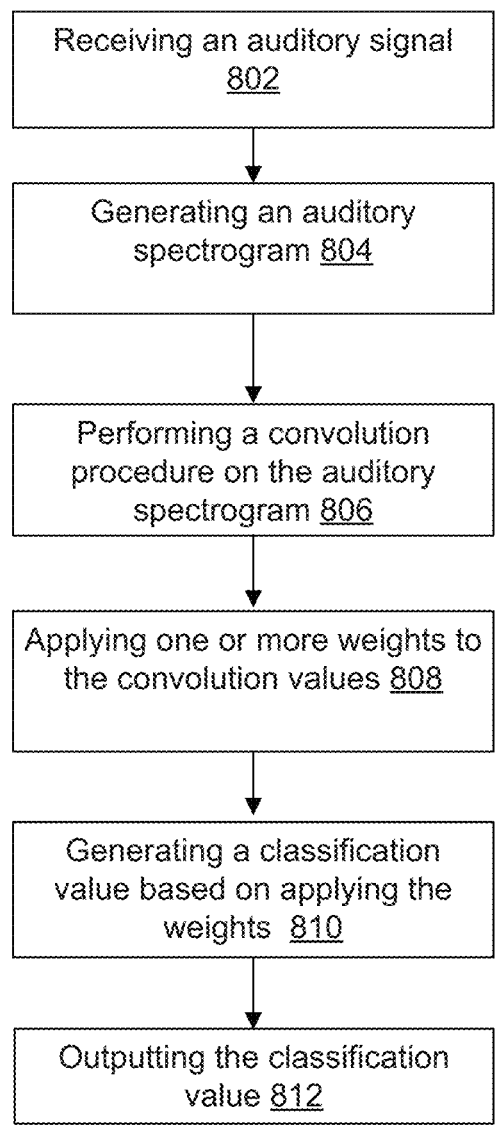
FIG. 8 is an exemplary method of operating the computing system in an embodiment of the present invention.

Referring now to FIG. 8, therein is shown an exemplary method 800 of operating the system 100 in an embodiment of the present invention. The method 800 includes: receiving, from a microphone, an auditory signal as shown in box 802; generating an auditory spectrogram based on the auditory signal as shown in box 804; performing a convolution procedure on the auditory spectrogram to generate one or more convolution values, wherein the convolution values represent a compressed version of a portion of the auditory spectrogram, and wherein the convolution procedure is trained to generate one or more features for detecting the respiratory abnormality as shown in box 806; applying one or more weights to the convolution values, wherein the weights are trained for detection of the respiratory abnormality as shown in box 808; generating a classification value based on applying the weights to the convolution values, wherein the classification value indicates whether the auditory signal includes the respiratory abnormality as shown in box 810; and outputting the classification value as shown in box 812.

Figure 9:
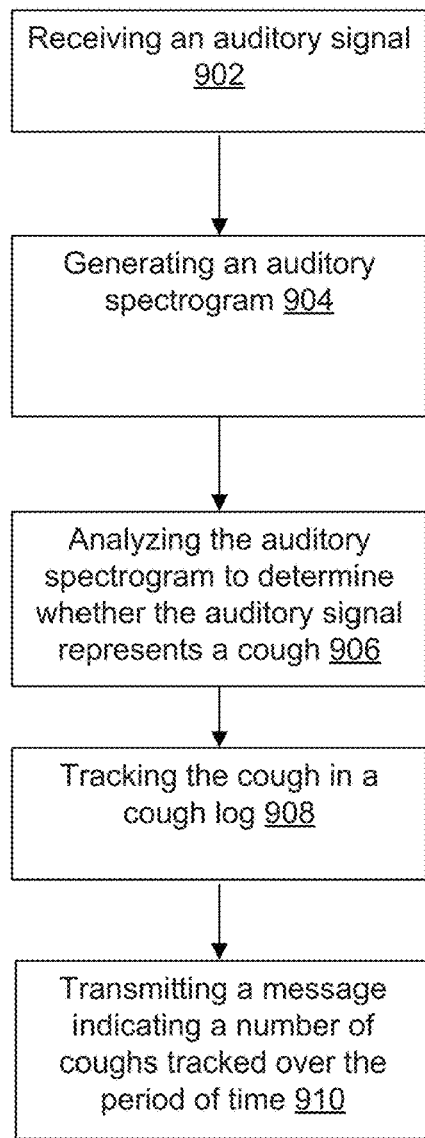
FIG. 9 is a further exemplary method of operating the system in an embodiment of the present invention.

Referring now to FIG. 9, therein is shown a further exemplary method 900 of operating the system 100 in an embodiment of the present invention. The method 900 includes: receiving, over a period of time from a microphone of a digital stethoscope, an auditory signal as shown in box 902; generating an auditory spectrogram based on the auditory signal as shown in box 904; analyzing, with a control unit of the digital stethoscope, the auditory spectrogram to determine whether the auditory signal represents a cough as shown in box 906; tracking, with the control unit of the digital stethoscope, the cough in a cough log as shown in box 908; and transmitting based on the cough log, with a communication unit of the digital stethoscope to a cloud-based service, a message indicating a number of coughs tracked over the period of time for storage on a remote server as shown in box 910.

Figure 10:
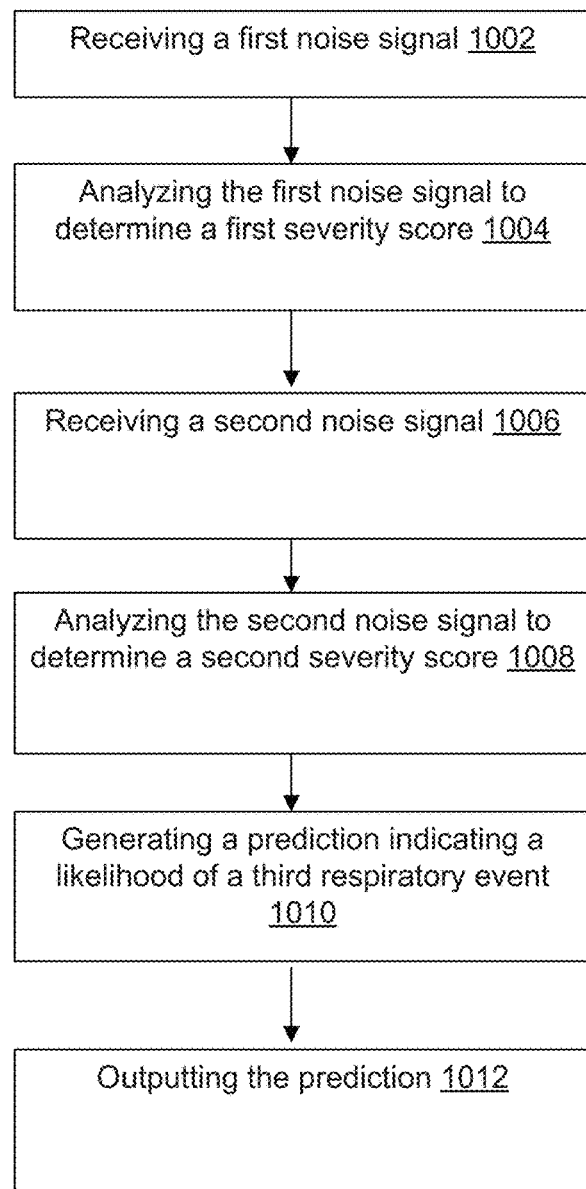
FIG. 10 is a further exemplary method of operating the system in an embodiment of the present invention.

Referring now to FIG. 10, therein is shown a further exemplary method 1000 of operating the system 100 in an embodiment of the present invention. The method 1000 includes: receiving, from a microphone of a digital stethoscope, a first noise signal at a first time as shown in box 1002; analyzing the first noise signal to determine a first severity score indicating how severe a first respiratory event of a patient captured in the first noise signal is as shown in box 1004; receiving, from the microphone of the digital stethoscope, a second noise signal captured at a second time as shown in box 1006; analyzing the second noise signal to determine a second severity score indicating how severe a second respiratory event of the patient captured in the second noise signal is as shown in box 1008; generating a prediction indicating a likelihood of a third respiratory event occurring for the patient at a future time based on applying a first weight to the first severity score and a second weight to the second severity score, wherein the first and second weights are trained based on a history of respiratory events as shown in box 1010; outputting the prediction as shown in box 1012.

Figure 11:
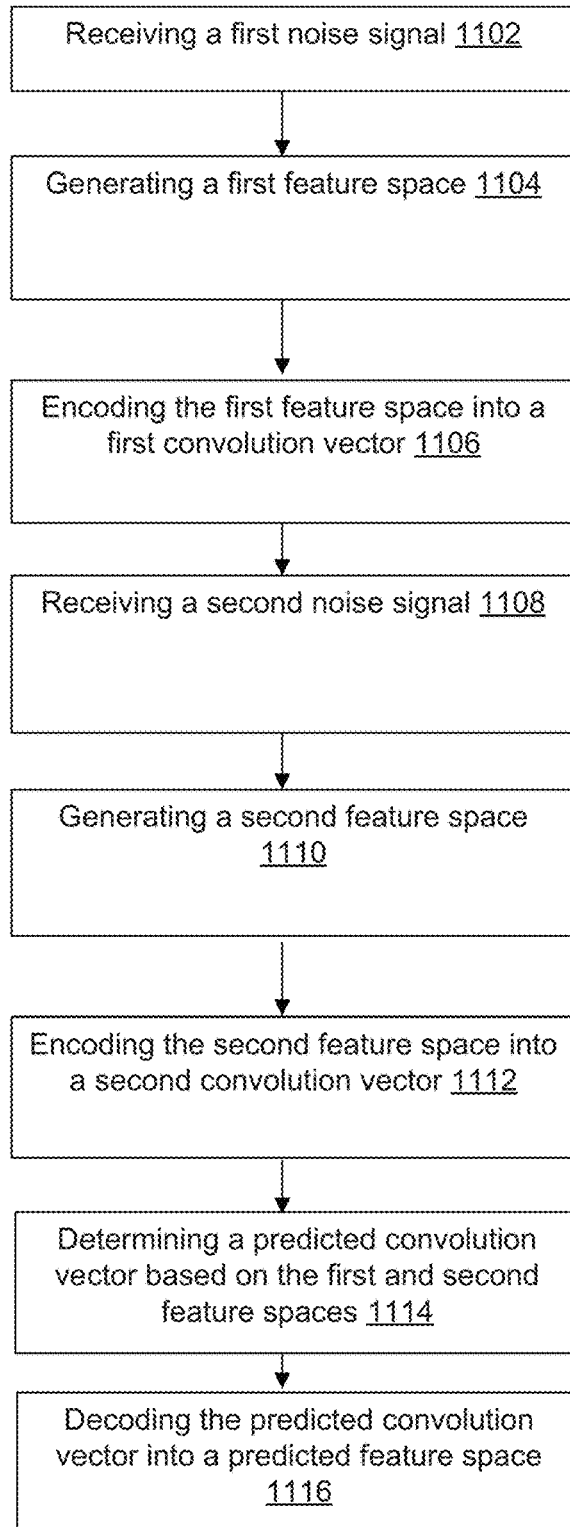
FIG. 11 is a further exemplary method of operating the system in an embodiment of the present invention.

Referring now to FIG. 11, therein is shown a further exemplary method 1100 of operating the system 100 in an embodiment of the present invention. The method 1100 includes: receiving, from a microphone of a digital stethoscope, a first noise signal capturing a first respiratory event at a first time as shown in box 1102; generating a first feature space representing the first noise signal as shown in box 1104; encoding the first feature space into a first convolution vector using a convolution procedure as shown in box 1106; receiving, from the microphone of the digital stethoscope, a second noise signal capturing a second respiratory event at a second time as shown in box 1108; generating a second feature space representing the second noise signal as shown in box 1110; encoding the second feature space into a second convolution vector using the convolution procedure as shown in box 1112; determining a predicted convolution vector based on the first and second feature spaces as shown in box 1114; and decoding the predicted convolution vector into a predicted feature space representing a sound made by the future respiratory event as shown in box 1116.

OTHER EXAMPLES AND EMBODIMENTS

Figure 12:
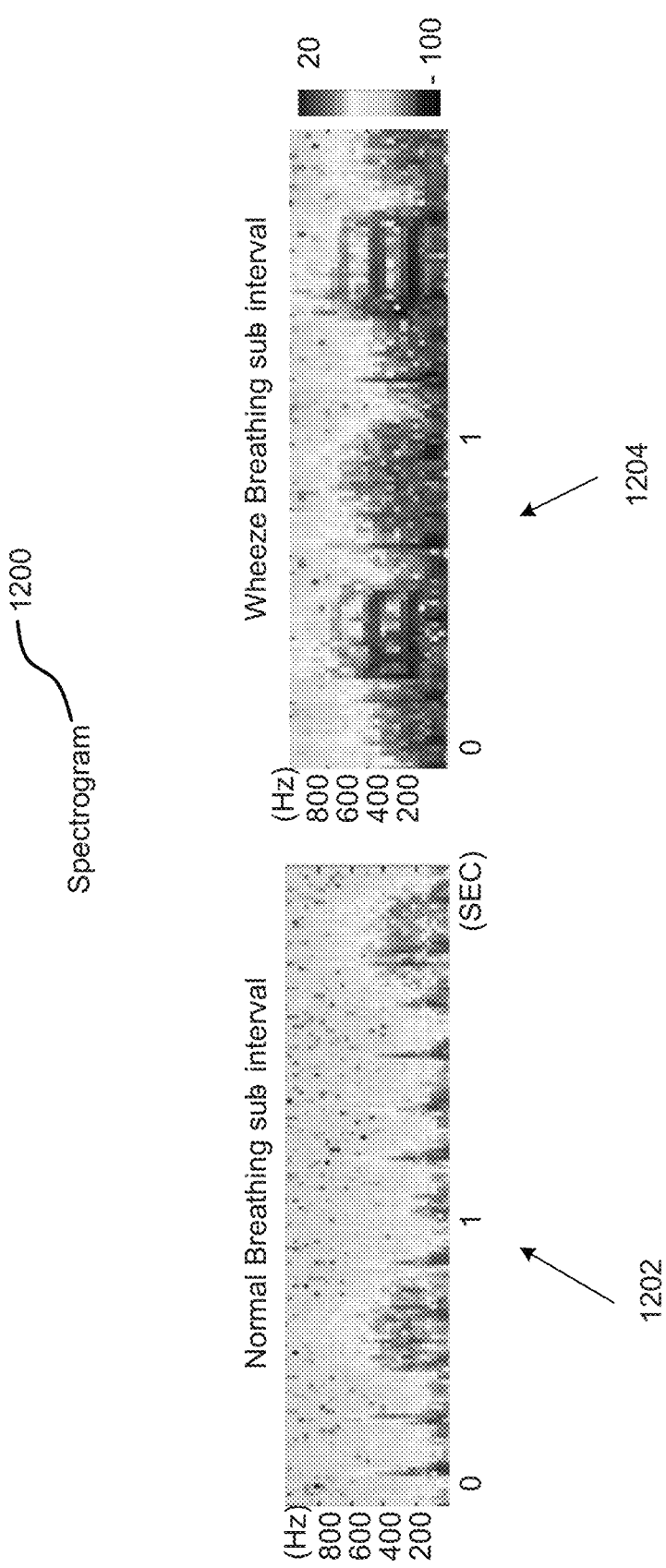
FIG. 12 depicts exemplary spectrograms representing breathing patterns in an embodiment of the present invention.
Figure 13:
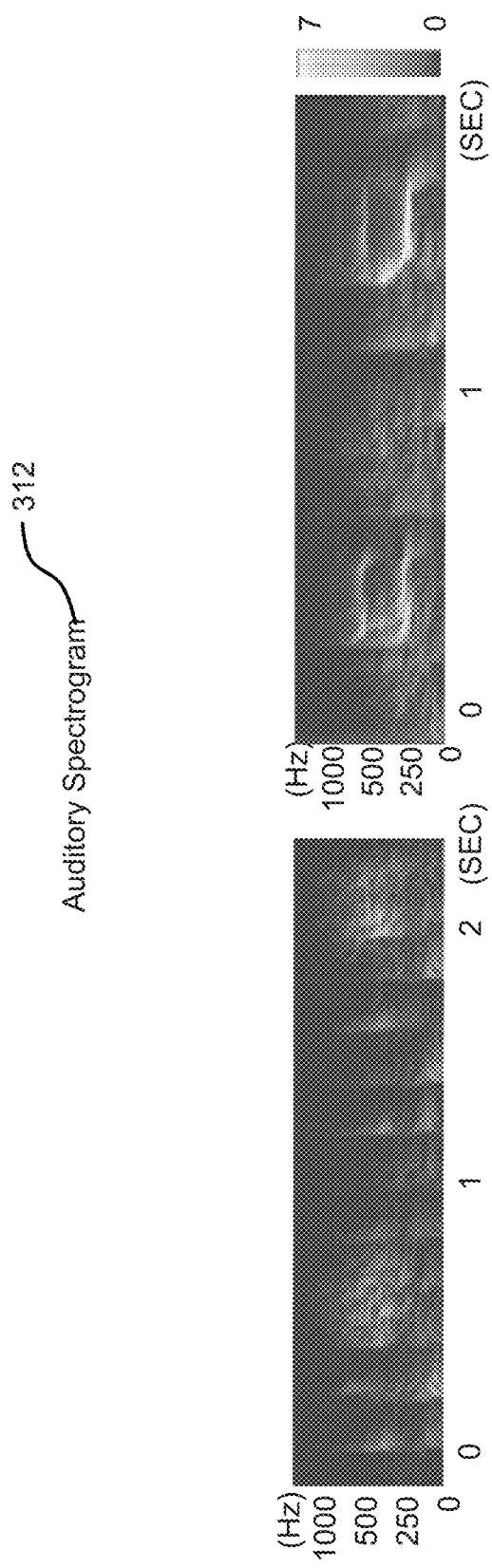
FIG. 13 depicts an exemplary auditory spectrogram in an embodiment of the present invention.

Referring now to FIG. 12, therein is shown exemplary spectrograms 1200 representing breathing patterns in an embodiment of the present invention. The spectrograms 1200 of FIG. 12, similar to what was described with respect to the auditory spectrogram 312 of FIG. 3, are two dimensional visual representations of the spectrum of frequencies of known noises, from the patient's body, for example a cough, a crackle, a wheeze, a breathing pattern, or a combination thereof. FIG. 12 shows two spectrograms 1200 representing two different breathing patterns, one for a normal breathing pattern 1202, indicating no respiratory abnormality, and one for a wheeze breathing pattern 1204, indicating a respiratory abnormality associated with a wheeze. In one embodiment, the breathing patterns and their representations in the form of the spectrograms 1200 can be used as a part of the back propagation process, as described with respect to FIGS. 3 and 5, to train the weights 276 and biases 334 of the machine learning processes used by the system 100 which are used by the system 100 to perform the detection of the respiratory abnormality, or to predict a respiratory event or respiratory condition in the future. For example, the spectrograms 1200 can be used to train the weights 276 and biases 334 used in the neural network 326, the LSTM process 514, or a combination thereof by for example using the spectrograms 1200 as examples of known breathing patterns which the system 100 can attempt to reconstruct through back propagation, and in the process determine the values of the weights 276 and biases 334 to reconstruct the spectrograms 1200. The biases 334 and weights 276 can subsequently be used to make future predictions about auditory signals 262 and classify them, by for example, classifying them as "normal" or "abnormal" based on the processes previously described Referring now to FIG. 13, therein is shown an exemplary auditory spectrogram 312 in an embodiment of the present invention. FIG. 13 shows a depiction of the auditory spectrogram 312 as described with respect to FIG. 3. FIG. 13 further shows how the auditory spectrogram 312 amplifies and sharpens the frequency components of an auditory signal 262. For example, FIG. 13, shows the frequency components of an auditory signal 262 as white marks. Further, FIG. 13 shows the magnitude of the frequency components by indicating lighter shades of white for frequency components that comprise a larger portion of the auditory signal 262 for a given time.

Figure 14:
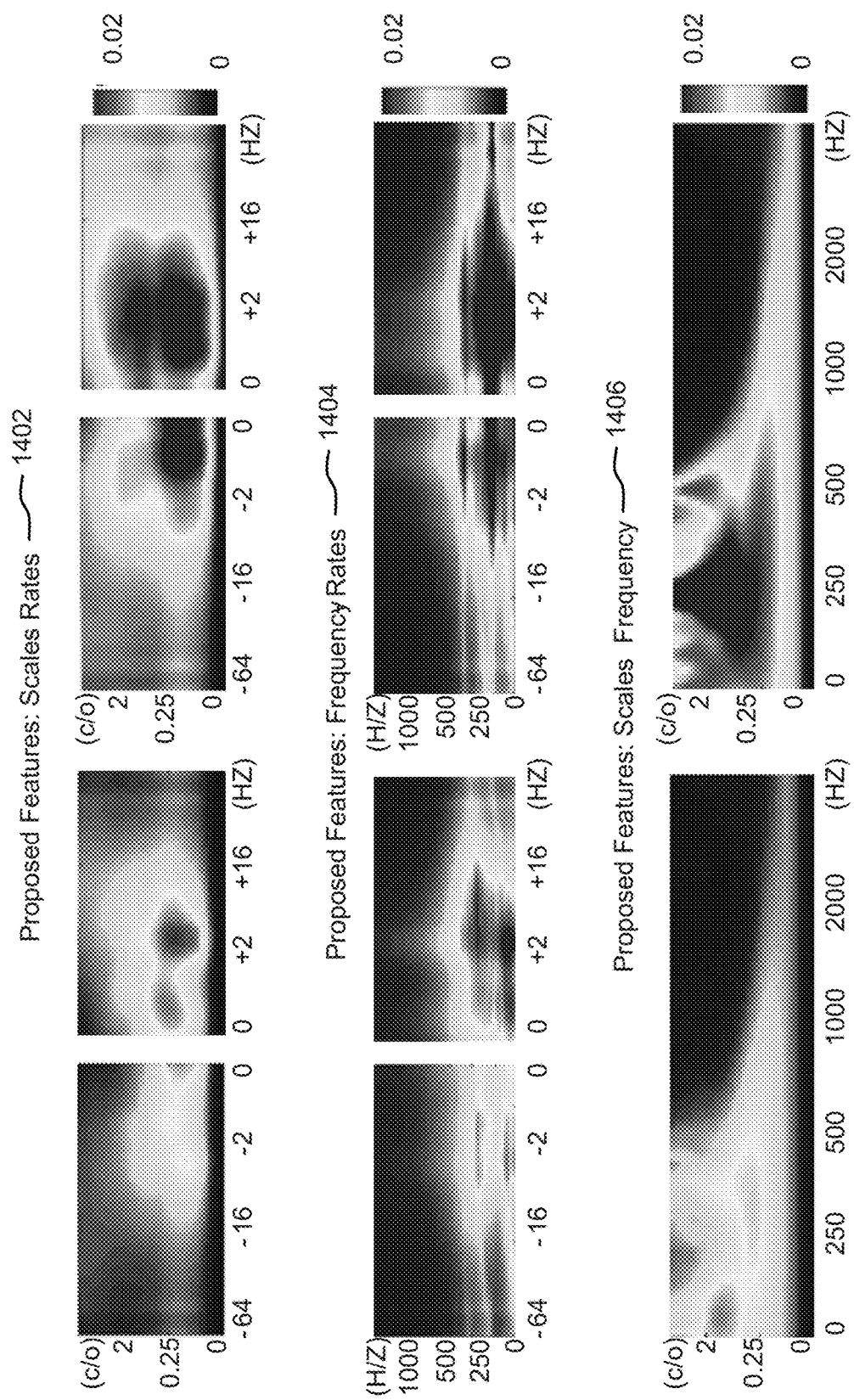
FIG. 14 depicts an exemplary feature space in an embodiment of the present invention.

Referring now to FIG. 14, therein is shown an exemplary feature space 602 in an embodiment of the present invention. FIG. 14 shows an exemplary frequency, rate, and scale of an auditory signals 262 at different times plotted against one another other. For clarity and ease of description, the frequency, rate, and scale are plotted as two dimensional visual representations where each of the frequency, rate, and scale is plotted against only one of the other variables, despite being described in FIGS. 6 and 7 as a three dimensional map or representation of the auditory signals 262. The combination of the plots of FIG. 14 represents the feature space 602. FIG. 14 further shows three plots 1402, 1404, and 1406. Plot 1402 represents a plot of the scale vs. rate. Plot 1404 represents a plot of frequency vs. rate. Plot 1406 represents a plot of scale vs. frequency. As described in FIGS. 6 and 7, the plots can be constructed and reconstructed to make the predictions regarding respiratory events or respiratory conditions in the future.

The above embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the above description, numerous specific details are given to provide a thorough understanding of the invention. However, it will be apparent that the invention may be practiced without these specific details. To avoid obscuring an embodiment of the present invention, some well-known circuits, system configurations, and process steps are not disclosed in detail.

The term "module" or "unit" referred to herein can include software, hardware, or a combination thereof in an embodiment of the present invention in accordance with the context in which the term is used. For example, the software can be machine code, firmware, embedded code, or application software. Also for example, the hardware can be circuitry, a processor, a microprocessor, a microcontroller, a special purpose computer, an integrated circuit, integrated circuit cores, a pressure sensor, an inertial sensor, a microelectromechanical system (MEMS), passive devices, or a combination thereof. Further, if a module or unit is written in the system or apparatus claims section below, the module or unit is deemed to include hardware circuitry for the purpose and the scope of the system or apparatus claims.

The modules and units in the following description of the embodiments can be coupled to one another as described or as shown. The coupling can be direct or indirect, without or with intervening items between coupled modules or units. The coupling can be by physical contact or by communication between modules or units.

The above detailed description and embodiments of the disclosed system 100 are not intended to be exhaustive or to limit the disclosed system 100 to the precise form disclosed above. While specific examples for the system 100 are described above for illustrative purposes, various equivalent modifications are possible within the scope of the disclosed system 100, as those skilled in the relevant art will recognize. For example, while processes and methods are presented in a given order, alternative implementations may perform routines having steps, or employ systems having processes or methods, in a different order, and some processes or methods may be deleted, moved, added, subdivided, combined, or modified to provide alternative or sub-combinations. Each of these processes or methods may be implemented in a variety of different ways. Also, while processes or methods are at times shown as being performed in series, these processes or blocks may instead be performed or implemented in parallel, or may be performed at different times.

The resulting method, process, apparatus, device, product, and system is cost-effective, highly versatile, and accurate, and can be implemented by adapting components for ready, efficient, and economical manufacturing, application, and utilization. Another important aspect of an embodiment of the present invention is that it valuably supports and services the historical trend of reducing costs, simplifying systems, and increasing performance.

These and other valuable aspects of the embodiments of the present invention consequently further the state of the technology to at least the next level. While the invention has been described in conjunction with a specific best mode, it is to be understood that many alternatives, modifications, and variations will be apparent to those skilled in the art in light of the descriptions herein. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A computer-implemented method of counting coughs for a patient comprising:
   receiving, over a period of time from a microphone of a digital stethoscope, an auditory signal;
   generating, with a control unit of the digital stethoscope, an auditory spectrogram based on the auditory signal, wherein the auditory spectrogram comprises a representation of a spectrum of frequencies of the auditory signal filtered by frequency domain functions;
   analyzing, with the control unit of the digital stethoscope, the auditory spectrogram to determine that the auditory signal represents a cough;
   tracking, with the control unit of the digital stethoscope, the cough in a cough log; and
   transmitting based on the cough log, with a communication unit of the digital stethoscope to a cloud-based service to detect a respiratory abnormality, a message indicating a number of coughs tracked over the period of time for storage on a remote server.

2. The method of claim 1 further comprising:
   receiving a further auditory signal collected contemporaneously with the auditory signal, from a further microphone of the digital stethoscope, wherein the further auditory signal represents a background noise; and
   adjusting, with the control unit, before analyzing the auditory spectrogram, the auditory signal based on the further auditory signal to reduce the background noise.

3. The method of claim 1 further comprising filtering, using one or more cochlear filters, the auditory signal according to a cochlear model before generating the auditory spectrogram, wherein the cochlear model is a mathematical model representing one or more frequency ranges a mammalian cochlea can hear.

4. The method of claim 3 further comprising:
   dividing, with the control unit, the auditory signal into one or more frequency bands; and wherein
   filtering, using the one or more cochlear filters, the auditory signal according to the cochlear model is based on filtering the one or more frequency bands.

5. The method of claim 1 wherein analyzing the auditory spectrogram includes applying a machine learning process trained using a set of respiratory noises annotated to identify the cough.

6. The method of claim 5 wherein analyzing the auditory spectrogram includes:
   performing a convolution procedure on the auditory spectrogram to generate a plurality of convolution values, wherein the convolution values represent a compressed representation of a portion of the auditory spectrogram, and wherein the convolution procedure is trained to generate one or more features for detecting the cough; applying one or more weights to the convolution values, wherein the weights are predetermined values for detection of the cough; and generating a classification value based on applying the weights to the convolution values, wherein the classification value indicates that the auditory signal includes the cough.

7. The method of claim 6 wherein the convolution procedure is performed repeatedly to successively compress the auditory spectrogram into a convolutional matrix to generate the convolution values.

8. The method of claim 1 further comprising predicting a future respiratory event based on the number of coughs tracked over the period of time.

9. A non-transitory computer readable medium including instructions for counting coughs for a patient comprising:
   receiving, over a period of time from a microphone of a digital stethoscope, an auditory signal;
   generating, with a control unit of the digital stethoscope, an auditory spectrogram based on the auditory signal, wherein the auditory spectrogram comprises a representation of a spectrum of frequencies of the auditory signal filtered by frequency domain functions;
   analyzing, with the control unit of the digital stethoscope, the auditory spectrogram to determine that the auditory signal represents a cough;

tracking, with the control unit of the digital stethoscope, the cough in a cough log; and transmitting based on the cough log, with a communication unit of the digital stethoscope to a cloud-based service to detect a respiratory abnormality, a message indicating a number of coughs tracked over the period of time for storage on a remote server.

10. The non-transitory computer readable medium of claim 9 with instructions further comprising:

receiving a further auditory signal collected contemporaneously with the auditory signal, from a further microphone of the digital stethoscope, wherein the further auditory signal represents a background noise; and adjusting, with the control unit, before analyzing the auditory spectrogram, the auditory signal based on the further auditory signal to reduce the background noise.

11. The non-transitory computer readable medium of claim 9 with instructions further comprising filtering, using one or more cochlear filters, the auditory signal according to a cochlear model before generating the auditory spectrogram, wherein the cochlear model is a mathematical model representing one or more frequency ranges a mammalian cochlea can hear.

12. The non-transitory computer readable medium of claim 11 with instructions further comprising:

dividing, with the control unit, the auditory signal into one or more frequency bands; and wherein filtering, using the one or more cochlear filters, the auditory signal according to the cochlear model is based on filtering the one or more frequency bands.

13. The non-transitory computer readable medium of claim 9 with instructions analyzing the auditory spectrogram includes applying a machine learning process trained using a set of respiratory noises annotated to identify the cough.

14. The non-transitory computer readable medium of claim 13 with instructions further comprising:

performing a convolution procedure on the auditory spectrogram to generate a plurality of convolution values, wherein the convolution values represent a compressed representation of a portion of the auditory spectrogram, and wherein the convolution procedure is trained to generate one or more features for detecting the cough; applying one or more weights to the convolution values, wherein the weights are predetermined values for detection of the cough; and generating a classification value based on applying the weights to the convolution values, wherein the classification value indicates that the auditory signal includes the cough.

15. The non-transitory computer readable medium of claim 14 with instructions wherein the convolution procedure is performed repeatedly to successively compress the auditory spectrogram into a convolutional matrix to generate the convolution values.

16. The non-transitory computer readable medium of claim 9 with instructions further comprising predicting a future respiratory event based on the number of coughs tracked over the period of time.

17. A digital stethoscope for counting coughs for a patient comprising:

a microphone configured to receive an auditory signal over a period of time; a control unit, coupled to the microphone, configured to:

analyze the auditory signal to determine that the auditory signal represents a cough indicative of a respiratory abnormality: generate an auditory spectrogram based on the auditory signal, wherein the auditory spectrogram comprises a representation of a spectrum of frequencies of the auditory signal filtered by frequency domain functions: track the cough in a cough log; and a communication unit, coupled to the control unit, configured to transmit, based on the cough log, a message to a cloud-based service indicating a number of coughs tracked over the period of time for storage on a remote server to detect the respiratory abnormality.

\* \* \* \* \*